(12) United States Patent
Banerjee et al.

(10) Patent No.: US 7,625,765 B2
(45) Date of Patent: Dec. 1, 2009

(54) DIRECTED ASSEMBLY OF FUNCTIONAL HETEROSTRUCTURES

(75) Inventors: Sukanta Banerjee, North Brunswick, NJ (US); Kairali Podual, North Brunswick, NJ (US); Michael Seul, Fanwood, NJ (US)

(73) Assignee: Bio Array Solutions Ltd., Warren, NJ (US)

( * ) Notice: Subject to any disclaimer, the term of this patent is extended or adjusted under 35 U.S.C. 154(b) by 309 days.

(21) Appl. No.: 11/253,452

(22) Filed: Oct. 19, 2005

(65) Prior Publication Data

US 2006/0068447 A1     Mar. 30, 2006

(51) Int. Cl.
*G01N 33/551* (2006.01)
(52) U.S. Cl. .................. 436/524; 428/306; 428/309; 428/323; 435/180; 435/181; 436/518; 436/527; 436/533; 436/534
(58) Field of Classification Search .................. 436/518, 436/524, 527, 533; 428/306, 309, 323; 435/4, 435/6, 7.1, 176, 180, 181, 261
See application file for complete search history.

(56) References Cited

U.S. PATENT DOCUMENTS

| | | | |
|---|---|---|---|
| 5,266,238 A | 11/1993 | Haacke et al. | |
| 5,281,370 A | 1/1994 | Asher et al. | |
| 5,552,270 A | 9/1996 | Khrapko et al. | |
| 5,770,721 A | 6/1998 | Ershov et al. | |
| 5,773,178 A * | 6/1998 | Shiota et al. | 430/20 |
| 6,143,499 A | 11/2000 | Mirzabekov et al. | |
| 6,251,691 B1 | 6/2001 | Seul | |
| 6,485,703 B1 * | 11/2002 | Cote et al. | 424/9.1 |
| 6,730,515 B2 | 5/2004 | Kocher | |
| 6,887,701 B2 | 5/2005 | Anderson et al. | |
| 2001/0007775 A1 * | 7/2001 | Seul et al. | 436/534 |
| 2001/0018164 A1 * | 8/2001 | Furukawa | 430/287.1 |
| 2001/0019405 A1 * | 9/2001 | Herron et al. | 356/39 |

(Continued)

FOREIGN PATENT DOCUMENTS

WO     WO 97/40385 A1     10/1997

(Continued)

OTHER PUBLICATIONS

Proudnikov, D. et al, "Immobilization of DNA in Polyacrylamide Gel for the Manufacture of DNA and DNA-Oligonucleotide Microchips", Analytical Biochemistry, vol. 259, pp. 34-41 (1998).

(Continued)

*Primary Examiner*—N Yang
(74) *Attorney, Agent, or Firm*—Eric P. Mirabel

(57) ABSTRACT

The present invention relates to a systematic process for the creation of functionally organized, spatially patterned assemblies polymer-microparticle composites including the AC electric field-mediated assembly of patterned, self supporting organic (polymeric) films and organic (polymeric)-microparticle composite films of tailored composition and morphology; the present invention further relates to the incorporation of said assemblies into other structures. The present invention also relates to the application of such functional assemblies in materials science and biology. Additional areas of application include sensors, catalysts, membranes, micro-reactors, smart materials. Miniaturized format for generation of multifunctional thin films. Provides a simple set-up to synthesize thin films of tailored composition and morphology.

23 Claims, 20 Drawing Sheets

Flip gel with exposed microparticles

U.S. PATENT DOCUMENTS

2001/0021377 A1* 9/2001 Jamiolkowski et al. ..... 424/78.36
2002/0166766 A1 11/2002 Seul et al.
2003/0082587 A1 5/2003 Seul et al.

FOREIGN PATENT DOCUMENTS

WO        WO 01/98765 A1    12/2001

OTHER PUBLICATIONS

Chen, G. et al., "pH-Sensitive Thin Hydrogel Microfabricated by Photolithography", Langmuir, vol. 14, pp. 6610-6612 (1998).
Gelfi, C. et al., "Investigation of the Properties of Novel Acrylamido Momomers by Capilary Zone Electrophoresis", Journal of Chromatography, vol. 608, pp. 333-341 (1992).
Warren, J. A. "Selected Spacings During Directional Solidification of a Binary Alloy", Spatio-Temporal Patterns, Ed. P.E. Cladis and P. Palffy-Muhoray, SFI Studies in the Science of Complexity, Addison-Wesley, pp. 91-105 (1995).
Ito, Y. et al. "Patterned Immobilization of Thermoresponsive Polymer", Langmuir, vol. 13, pp. 2756-2759, (1997).
Otero, T. F. et al. "Electrochemically initiated acryllic acid/acrylamide copolymerization", J. Electroanal. Chem., vol. 256, pp. 433-439, (1988).
Beebe, D. J. et al. "Functional hydrogel structures for autonomous flow control inside microfluidic channels", Nature, vol. 404, pp. 588-590.
Liang, L. et al. "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11, (1999).
Kim E., et al. "Polymer microstructures formed by moulding in capillaries", Nature, vol. 376, pp. 581-584, (1995).
Otero T. F., et al. "Electroinitiated polymerization of acrylamide in DMF: Attempts at an interfacial model", J. Electroanal. Chem., vol. 304, pp. 153-170, (1991).
Righetti, P. G. et al. "Electrophoresis gel media: the state of the art", Journal of Chromatography B, vol. 699, pp. 63-75 (1996).
Tanaka T. et al., "Mechanical Instability of gels at the phrase transition", Nature, vol. 325, pp. 796-798, (1987).
L. Liang et al. "Temperature-sensitive membranes prepared by UV photopolymerization of N-isopropylacrylamide on a surface of porous hydrophilic polypropylene membranes", Journal of Membrane Science, vol. 162, pp. 235-246 (1999).
Holtz, J., et al., "Intelligent Polymerized Crystalline Colloidal Arrays: Novel Sensor Materials", Analytical Chemistry, vol. 70, No. 4, pp. 780-791, (1998).
Kumacheva, E. et al., "Three-dimensional Arrays in Polymer Nanocomposites", Advanced Materials, vol. 11, No. 3, pp. 231-234, (1999).
K Vorlop, K. D., et al., "Entrapment of Microbial Cells Within Polyurethane Hydrogel Beads with the Advantage of Low Toxicity", Biotechnology Techniques, vol. 6, No. 6, pp. 483-488, (1992).
LaForge, K. S. et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction", American Journal of Medical Genetics (Neuropsychiatric Genetics) vol. 96, pp. 604-615, (2000).
Yershov G., et al., "DNA analysis and diagnostics on oligonucleotide microchips", Proceedings of the National Academy of Sciences USA, vol. 93, pp. 4913-4918 (1996).
Kalinina O. et al., "A 'Core-Shell' Approach to Producing 3D Polymer Nanocomposites", Macromolecules, vol. 32, pp. 4122-4129, (1999).
Jackman, R. J. et al., "Using Elastomeric Membranes as Dry Resists and for Dry Lift-Off", Langmuir vol. 15, pp. 2973-2984.
Jeon, N. L. et al., "Patterned polymer growth on silicon surfaces using microcontact printing and surface-initiated polymerization", Applied Physics Letters, vol. 75, No. 26, pp. 4201-4203 (1999).
Y. Iwayama, et al., "Optically Tunable Gelled Photonic Crystal Covering Almost the Entire Visible Light Wavelength Region." Langmuir, 2002.
S.R. Dziennik, et al., "Nondiffusive mechanisms enhance protein uptake in ion exhange particles." PNAS, 2003: 420-425. vol. 100, No. 2.
A. Hatch, et al., "Diffusion Immunoassay in Polyacrylamide Hydrogels," Micro Totals Analysis Systems, 2001: 571-572.
N. Fatin-Rouge, et al. "Diffusion and Partitioning of Solutes in Agarose Hydrogels: The Relative Influence of Electrostatic and Specific Interactions". J. Phys. Chem. B., 2003; 12125-12137, vol. 107.
P. Krsko et al. "Electron-Beam Surface-Patterned Poly(ethylene glycol) Microhydrogels", Langmuir, 2003: 5613-5625, vol. 19.
P. Ghosh, et al. "A Simple Lithographic Approach for Preparing Patterned Micron-Scale Corrals for Controlling Cell Growth." Angew. Chem. Int. Ed., 1999; 1592-1595, vol. 38, No. 11.
W.G. Koh, et al. "Poly(ethylene glycol) Hydrogel Microstructures Encapsulating Living Cells," Langmuir, 2002: 2459-2462, vol. 18.
W.G. Koh, et al. "Molding of Hydrogel Microstructures to Create Multiphenotype Cell Microarrays," Analytical Chemistry, 2003.
C. Bandeira-Melo et al. "EliCell, a gel-phase dual antibody capture and detection assay to measure cytokine release from easinophils," Journal of Immunological Methods, 2000: 105-115, vol. 244.
One Cell System Product Information, http://www.onecell.com/AboutUs.htm.
Sentek Group, Inc. Product Information, http://www.sentekgroup.com/glucoview.htm.

* cited by examiner

Flip gel with exposed microparticles

Assay Format

Assay Result

Assay Format

Assay result

DIRECTED ASSEMBLY OF FUNCTIONAL HETEROSTRUCTURES

CROSS-REFERENCE TO RELATED APPLICATION

The present application is based on and claims priority of U.S. Provisional Application No. 60/300,025, filed Jun. 21, 2001, which is incorporated herein by reference in its entirety.

BACKGROUND OF THE INVENTION

A longstanding objective within the materials, engineering, biomedical and analytical sciences has been the design of ever-smaller structures and devices for use in miniaturize systems capable of performing specific functions, such as sensors, transducers, signal processors or computers. Of particular interest as potential building blocks in this context have been functional materials having predetermined properties. Patterned films composed of suitable polymers and polymer-microparticle composite films offer particularly attractive opportunities to realize hierarchically organized structures of functional materials and to provide confinement and segregation for performing "local" chemical reactions.

Several methods of preparing patterned polymer films and polymer-microparticle composite films have been described. In one example, polymer molding has been used to prepare polymeric films. Beginning with a master that is fabricated from a silicon (Si) wafer using conventional lithographic techniques, a mold is made using an elastomer such as polydimethylsiloxane (PDMS). The mold is then used to produce replicas in a UV-curable polymer such as polyurethane. The applicability of this technique of polymer molding, long used for replication of micron-sized structures in devices such as diffraction gratings, compact disks, etc., recently has been extended to nanoscale replication (Xia, Y. et al., Adv. Mater. 9: 147 (1997), Jackman, R. J. et al., Langmuir. 15:2973 (1999), Kim, E. et al. Nature 376, 581 (1999).

Photolithography has been used to produce patterned, stimuli-sensitive polymeric films which can be further functionalized with bioactive molecules and which undergo abrupt changes in Volume in response to changes in pH and temperature (Chen, G. et al., Langmuir. 14:6610. (1998); Ito, Y. et al., Langmuir 13: 2756 (1997)). UV-induced patterned polymerization of various hydrogel structures within microchannels has been described as a means for the autonomous control of local flow (Beebe, D. J. et al., Nature., 404:588 (2000)).

Surface-initiated ring-opening metathesis polymerization following microcontact printing has been used to create patterned polymer layers which remain attached to the surface and produce structures of controlled vertical and lateral dimensions (Jeon, N. L. et al., Appl. Phys. Lett. 75:4201 (1999)). Other techniques such as thermal radical polymerization (Liang, L., J. Appl. Polym. Sci. 72:1, (1999)) and UV-induced polymerization (Liang, L., J. Membr. Sci. 162: 235 (1999)) have been used to generate surface confined thin, uniform and stimuli-sensitive polymeric films.

Sarasola, J. M. et al. (J. Electroanal. Chem. 256:433, (1988) and Otero, T. F. et al., J. Electroanal. Chem. 304:153, (1991) describe electropolymerization of acrylamide gels using Faradaic process. Acryluminde gels are prepared on electrode surfaces by an anodic oxidative polymerization process using the electroactive nature of acrylamide monomers.

Polymerization of crosslinked acrylamide has been described to produce a matrix of glass-immobilized polyacrylamide pads which were activated with receptor molecules of interest including oligonucleotides or proteins. The use of the resulting porous and highly hydrated matrix for simultaneous monitoring of ligand-receptor binding reactions has been reported (Proudnikov, D. et al., Anal. Biochem. 259:34 (1998); Yershov, G., Proc. Natl. Acad. Sci. U.S.A. 93:4913 (1996), LaForge, S. K., Am. J. Med. Genet. 96:604 (2000); Khrapko, K. R. et al. U.S. Pat. No. 5,552,270, 1996; Ershov, G. M. et al. U.S. Pat. No. 5,770,721, 1998; Mirzabekov et al. U.S. Pat. No. 6,143,499.).

A process for the assembly of a 3-D array of particles has been described which is based on the synthesis of a core-shell latex particle containing a core polymer with a glass transition temperature significantly higher than that of the shell polymer. In accordance with that process, particles were assembled into a 3-D close packed structure and annealed in such a way that the core particle remained unaltered while the shell polymer flowed, resulting in a continuous matrix embedding an organized 3-D array of core particles (Kalinina, O. and Kumacheva, E., Macromolecules. 32:4122 (1999); Kumacheva, E. et al., Adv. Mater. 11:231 (1999), Kumacheva, E. et al., U.S. Pat. No. 5,592,131 (1999)).

The encapsulation of a colloidal crystalline array within a thin, environmentally sensitive hydrogel matrix capable of swelling in response to changes in pH and temperature has been described. In other instances, the hydrogel contained immobilized moieties capable of triggering the swelling of the gel in the presence of particular analytes. The swelling of the gel matrix increases the periodicity of the colloidal crystal array and produces a shift in Bragg diffraction peaks in the spectra of the scattered light (Holtz, J. H. et al., Anal. Chem. 70:780 (1998); Haacke, G. et al., U.S. Pat. No. 5,266,238, 1993; Asher, S. A., U.S. Pat. No. 5,281,370, 1994). The process of forming the colloid crystal relies on passive diffusive transport of particles within the prepolymer reactive mixture.

Each of the aforementioned references are incorporated herein by reference in its entirety.

SUMMARY OF THE INVENTION

The present invention provides a systemic synthetic process to translate a sequence of synthetic instructions into a sequence of synthetic operations that are performed in a homogenous fluid phase, to produce patterned polymeric films, functional polymeric films, multicomponent microparticle assemblies and/or polymer-microparticle film composites of pre-determined composition, layout and morphology. Rather than arranging individual molecules by explicit external placement, this approach combines dynamically controlled "self-assembly" and triggered polymerization process to realize heterostructures of preconceived architecture and design.

In one aspect, the present invention provides methods and apparatus for assembling particles at preset times and in pre-designated positions on a substrate surface and to mediate the transformation of thin, patterned gel films. The present invention thus permits a sequence of multiple reaction steps to be executed at preset times in accordance with an externally set schedules within a homogenous reaction, each step invoking an active transport or reaction process.

In another aspect, the present invention provides processes and apparatus for synthesis of patterned polymer films and/or polymer-microparticle film composites that are mediated by AC electric field. The present invention also relates to the incorporation of the gels and composites into other structures. The present invention further relates to the application of such gels and composites in material science and biology. Illustrative areas of application include: catalysts, smart materials, membranes, sensors and microreactors.

In contrast to some of the methods for producing functionalized polymeric films, the present invention does not require complex chemistries of limited applicability nor does it require multiple unrelated processing steps. Furthermore, in the case of polymer-microparticle film composite structures, the present invention does not rely on diffusive transport, a slow and environmentally sensitive process, in the assembly of ordered particle arrays.

BRIEF DESCRIPTION OF DRAWINGS

FIG. 2(*b*) is a photograph showing a free-standing gel film imaged in aqueous phase.

FIG. 3(*b*) is a photograph showing a monolithic gel-microparticle composite film created via UV-initiation.

FIG. 4(*b*) is an illustration showing a flipped gel-particle composite film with the particles partially exposed.

DETAILED DESCRIPTION OF THE INVENTION

Figure 1:
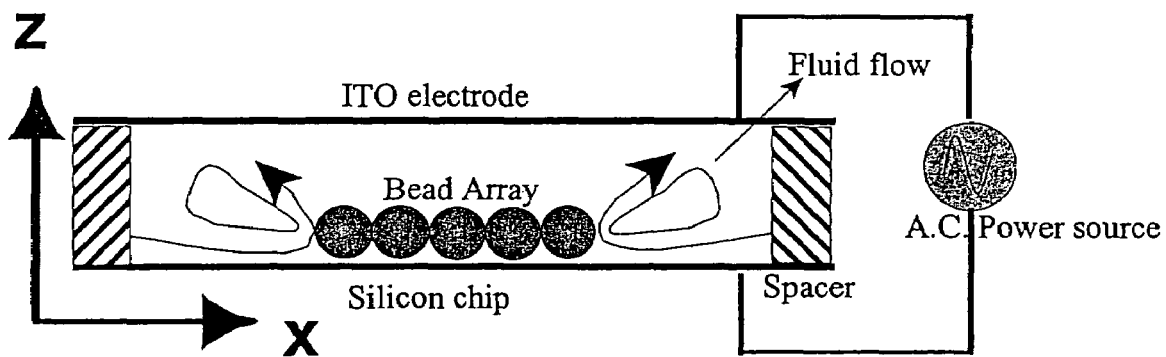
FIG. 1 is an illustration showing an experimental configuration for LEAPS.

The present invention provides methods for synthesis of patterned polymeric films and/or polymer-microparticle film composites that are simple in implementation and flexible in the choice of polymer chemistry used. Also provided is an apparatus useful in said methods. Patterned polymer films and polymer-microparticle film composites and their uses are also provided. The invention is based at least in part on the technology designated "LEAPS" (which refers to "Light-Controlled Electrokinetic Assembly of Particles near Surfaces).

In certain embodiments, the methods of the present invention combines the action of an active self-assembly process acting on long length scales such as LEAPS with externally triggered, template-directed gel chemistries to provide: the self-assembly of microparticle arrays in designated positions on a planar or substantially planar substrate, the externally directed, sequential execution of multiple assembly steps requiring a schedule of initiation and termination; and spatial confinement to enable concurrent execution of multiple assembly steps in different compartments. The resulting heterostructures exhibit an organization in accordance with a predesigned architecture to meet the requirements associated with the execution of specific functions. Applications of the process to the fabrication of functional materials, sensors and more generally chemical transducers and information processors also are of interest.

Light-Controlled Electrokinetic Assembly of Particles Near Surfaces

LEAPS technology relates to movement of particles and/or fluid suspended at an electrolyte solution-electrode interface and is described in detail in PCT International Application No. PCT/US97/08159 as well as in U.S. Ser. No. 09/397,793, filed Sep. 17, 1999; U.S. Ser. No. 09/320,274, filed May 28, 1999, and PCT International Application No. PCT/US00/14957; U.S. Ser. No. 09/813,571, filed Mar. 21, 2001; and PCT International Application No. PCT/US01/20179, filed Jun. 21, 2001. Each of these patents/patent applications is incorporated by reference in their entirety.

LEAPS involves the use of electrokinetic and polarization-induced forces which arise in accordance with the lateral impedance gradients at an interface between an electrolyte solution and an electrode to control fluid flow, particle transport and/or particle assembly.

In one embodiment of LEAPS, a plurality of particles are suspended in an interface between an electrolyte solution and a light sensitive electrode (e.g., a planar electrode). An AC electric field is generated at the interface and the interface is illuminated with a predetermined light pattern to assemble particles in the areas of the electrode designated by the pattern of illumination (e.g., regions of low impedance). Particles move to the low impedance area and form an assembly when the frequence of the applied electric field is less than the relaxation frequency of the particles. Accordingly, if the relaxation frequency of the particles are known, one can directly adjust the frequency of the electric field to form the particle assembly. If the relaxation frequency of the particles are not known, then the frequency of the applied AC field may be readily adjusted until the assembly occurs. If no particles are present in the interface, and the movement of the fluid is what is desired, that may be accomplished by adjusting the frequency of the applied electric field to be less than the relaxation frequency of the electrolyte solution-electrode interface.

In another embodiment of LEAPS, a patterned electrode is used instead of the light-sensitive electrode. For example, a first electrode is positioned in a first plane and a second electrode (preferably of planar geometry) is positioned in a second plane different from the first. The particles suspended in an electrolyte solution (or an electrolyte solution without the particles) are located between the first and the second electrode. The second electrode comprises a patterned electrode. The term "patterned electrode," as used herein, refers to an electrode having a surface and an interior, either or both of which are modified to produce spatial modulations in the properties of the second electrode that affects the local distribution of the electric field at the electrolyte solution-electrode interface. When the AC electric field is applied at the interface, the particles assemble in designated areas of the second electrode that are defined by the spatial modulations in the properties of that electrode (e.g., low impedance regions). In the absence of the particles, fluid movement may also be controlled by the application of AC field.

The electrode may patterned by a number of ways to affect the interfacial impedance. Preferably, the electrode is patterned by spatially modulated oxide growth, surface chemical patterning or surface profiling. If the patterned electrode is a light-sensitive electrode, the patterning in combination with the illumination pattern on said electrode may be used to control the movement of the particles and/or fluid at the solid-liquid interface.

In preferred embodiments, the patterned or light-sensitive electrode comprises a silicon electrode (e.g., silicon chip), which may also be coated with a dielectric layer. One such example is a Si/SiOx electrode. In one particularly preferred LEAPS configuration, an additional electrode is provided such that the light-sensitive (or the patterned electrode) and the additional electrode are substantially planar and parallel to one another and separated by a gap (e.g., in a sandwich configuration), with the electrolyte solution (with or without the particles) being located in the gap. The additional electrode preferably comprises an optically transparent electrode (e.g., ITO coated glass), which allows optical inspection of the movement of the particles and/or fluid at the interface. When such type of LEAPS cell is used, an AC electric field may be applied at the solid-liquid interface by applying an AC voltage between the light-sensitive (or patterned) electrode and the additional electrode.

When a plurality of particles are suspended in the electrolyte solution and subject to LEAPS, it is preferred that the particles form a planar assembly on the designated areas of the electrode, more preferably in an array configuration. However, the particles may also be assembled in a linear configuration or any other configuration that is dictated by the illumination pattern and/or patterning.

The term "particles" as used herein include colloidal particles, eukaryotic and prokaryotic cells, micells, vesicles (e.g., liposomes) and emulsion droplets. In preferred embodiment, the size of the particles range from about 0.2 to about 20 µm in diameter.

Formation of Patterned Polymeric Film

The present invention provides methods for synthesizing patterned polymeric film using the LEAPs technology described in the preceding section. In certain embodiments, a polymerization mixture comprising a monomer and an initiator in an electrolyte solution is provided. Preferably, the polymerization mixture also contains a cross-linker, with the monomer, initiator and the crosslinker dissolved in the electrolyte solution. This mixture is placed between the light-sensitive (or patterned) electrode and the additional electrode. An AC electric field is applied in the interface between the electrolyte solution and the light-sensitive (or patterned) electrode. Lateral impedance gradients at the interface, set up by the patterning or the predetermined pattern of illumination, give rise to local recirculating electro-osmotic fluid motion, which effectively transports fluid (and particles if they are present) from regions of high impedance to regions of low impedance. Depending on the initiators used, the application of the AC electric field, in addition to the illumination of the electrode with a predetermined light pattern (when light-sensitive electrode is used) or the patterning of the electrode, may be sufficient to induce formation of a patterned polymeric film on the low impedance regions of the light-sensitive or patterned electrode.

In preferred embodiments, the polymerization is triggered at a desired time by using initiators that are heat or photoactivated. If such a case, the polymerization mixture is heated or irradiated with UV-light to initiate polymerization. Heat-generated or UV-generated free radicals diffuse and react with monomers to produce initially oligomers and finally a crosslinked polymer film.

As the gel film grows, a moving reaction extends into the solution with time. In case of the heat-induced polymerization, polymerization starts from the light-sensitive or patterned electrode (e.g., silicon chip). Due to the presence of LEAPs-mediated, strong convective transport near the light-sensitive (or patterned) electrode surface, the polymerization process is triggered preferentially in the low impedance areas on that electrode, thereby giving rise to a spatially patterned polymeric film on said electrode. In case of UV-induced polymerization, however, polymerization starts at the additional electrode (usually the top electrode), and produces an unpatterned monolithic gel.

The present invention, in contrast to several known methods, do not require complex implementation, such as use of a mask, in preparation of patterned gel films. In addition, the methods of the present invention allow increased flexibility in choice of monomers, crosslinkers and initiators used. It should, however, be noted that high viscosity of the polymerization mixture and high ionic concentration may impede with the proper functioning of LEAPS by interfering with the interfacial fluid flow. Accordingly, it is recommended that the ionic concentration of the polymerization mixture be about 1.0 mM or lower, preferably between about 0.1 mM to 1.0 mM. This may be accomplished by selecting initiators to maintain low ionic concentration of the mixture. Initiators, as are monomers and crosslinkers, are well known in the art and may readily be obtained from commercial sources.

As for the monomers and crosslinkers, it is recommended that low viscosity monomers and crosslinkers be used, such that the viscosity of the polymerization mixture is about 100 cp or less. When the patterned film to be produced is a hydrogel, water-soluble monomers are preferred. In addition, when said film is optically transparent. The desired monomer concentration may be adjusted according to the type of gel to be produced (e.g., self-supporting or cleaved gel). In one embodiment, a mixture of acylamide and bisacrylamide of varying monomer concentrations, from about 20% to about 5%. (acylamide:bisacrylamide=37.5:1, molar ratio) may be used to produce a hydrogel. In preferred embodiments, the polymeric film obtained comprises a cross-linked alkylacrylamide or hydroxyalkymethacrylate hydrogel.

The AC voltage depends on the polymerization mixture and is readily adjusted until the desired polymeric film (or polymer-microparticle film composite) is formed. Preferably, the voltage applied is in the range of about 0.5 to about 15 V (peak to bead) and the frequency is preferably more than about 10 hz and less than about 500 kHz, more preferably about 1 kHz to 10 kHz.

In one embodiment of the invention, LEAPS is carried out in a fluidic microcell formed by sandwiching a double-sided Kapton sapcer of about 100 um thickness (between a 1 cm×1 cm silicon chip (n-typed, capped either by a uniform or a lithographically patterned thin SiO2 layer) and a glass cover slip coated with indium tin oxide (ITO) to a typical sheet resistance of 1400 Ohn square.

In preferred embodiments of the present invention, an electrolyte solution (more preferably, an aqueous solution) is used in the polymerization mixture, e.g., to dissolve monomers, crosslinkers and initiators. In certain embodiments, other polarizable liquid medium may be used, including non-aqueous solution. The relaxation frequency of the particles assembled in a non-aqueous solution (e.g., DMSO and acetonitrile) is shifted to lower values when compared with that of an aqueous solution.

The hydrogels of the present invention may be functionalized by variety of methods known in the art. For example, during the polymerization step itself small amounts of functional monomers may be introduced along with the polymerization mixture (e.g., acrylamide mixture). Acrylic acid, 2-hydroxyethylmethacrylate (HEMA), diethylaminoethylmethacrylate hydrochloride etc. could be incorporated into the hydrogel so that the micropatterned gel may be chemically addressed via the carboxy, hydroxy and amino functional groups. Biomolecules of interest may subsequently be immobilized in the gel using suitable chemistry and linker molecules.

Small probe molecules or functional co-monomers may also be introduced into the hydrogel using the same approach to yield novel sensor and stimuli responsive hydrogel structures, that can respond to a variety of inputs such a pH, temperature, electric field, light etc. Microscale structures made from such stimuli-responsive materials may act as an actuator, for example for controlling fluid flow (valve). Such structures will be self regulating and would not require an external power source.

Polymer-Microparticle Film Composites

By providing a plurality of particles suspended in the polymerization mixture, the methods for patterned polymeric film synthesis, as described in the preceding section, may be used to obtain an assembly of the particles embedded in a polymeric film (also referred to as "polymer-microparticle composite" or "heterostructure"). The composite formation is comprised of two stages. First, particle assemblies (e.g., planar particle assemblies, more preferably particle arrays) are formed from the particle suspension also containing all ingredients required for subsequent in-situ gel formation, as described previously. Second, a polymeric film is formed to produce the polymer-microparticle film composite. In one preferred embodiment, gels are formed by heat-initiated in-situ polymeriation to form a composite in which the gels are spatially patterned. In another preferred embodiment, the gels are formed by UV-initiated in-situ polymeriation to obtain a composite in which the gels are monolithic (not patterned).

In one embodiment, AC voltage of 1 to 20 V p-p in a frequency range of from about 100's of hertz to several kilohertz are applied between the electrodes across the fluid gap. Fluid and particle transport and assembly may be monitored by video microscopy permitting frame capture and digitation of frames for further analysis.

The thermal free radical polymerization may be initiated by heating the polymerization mixture (e.g., by heating the LEAPs cell), for example, to about 40 to 45 C, for about 1 to 10 minutes, using an IR lamp, while maintaining the AC electric field at the electrolyte solution-electrode interface, to form a patterned film or polymer-microparticle film composite.

The polymerization may also be triggered by irradiating the polymerization mixture with UV-light. For example, in the presence of the applied AC electric field, polymerization may be triggered by using a mercury lamp source. A wide range of wavelengths spanning from about 250 to 340 nm may be used, for about 15 seconds to about 10 minutes. In one preferred embodiment, the concentration of monmers in the polymerization mixture may be about 10% by weight, and 2-hydroxy-4'-hydroxyethoxy-2-methylpropiophenoe) may be used as the initiator to give a 1.5% by weight solution.

In certain embodiments, particles comprise beads (also referred to as "microparticles" or "microspheres") that are composed of silica, modified polystyrene or other polymers. Preferably, these particles are anionic or cationic particles ranging from about 0.5 µm to about 15 µm in diameter. In certain preferred embodiments, these particles are functionalized by attaching a variety of chemical functional groups to their surfaces. The process of forming composite gel-particle films may readily be extended to particles that display biomolecules attached on their surfaces, such as receptors or ligands. In certain embodiments, oligopeptides, proteins, oligonucleotides or nucleic acid fragments may also be attached to the particle surfaces. The particles may also be encoded by use of a chemically or physically distinguishable characteristic that are uniquely identifies the biomolecules attached to those particles, an example of which includes color encoding the particles using flourophore or chromophore dyes. Such a process allows chemical immobilization of functionalized microparticle assemblies or arrays for a variety of biochemical assays, including binding and functional assays. Examples 6 to 9 describe a number of these assays.

In certain embodiments, the particles used in preparing polymer-microparticle film composites may be magnetic particles. In certain other embodiments, the particles used are eukaryotic or prokaryotic cells, or liposomes. The polymer-microparticle film composites produced using these particles may also be used in various biochemically assays, including the assays described in Examples 12 to 16.

The particles useful in preparation of the polymer-particle film composite may also comprise inorganic particles, including metal particles, semiconductor particles and glass particles. The inorganic particles may also be coated with a polymeric shell.

Self-Supporting, Flipped and Cleaved Gels and Gel-Microparticle Films

Accordingly, the present invention provides novel patterned films and/or polymer-microparticle film composites, including a planar assembly or array of particles embedded in a gel (2-dimensional assembly). In preferred embodiment, these gels are prepared according to the methods described above.

As discussed previously, the patterned polymeric films and the polymer-microparticle film composites of various types may be produced, for example, by varying the monomer concentration.

In one embodiment of the present invention, a self-supporting film (preferably a hydrogel) is prepared. In one example, the concentration of monomers in the polymerization is greater than about 10% by weight. Preferably, acrylamide monomers are used. Following the polymerization, the LEAPS microcell may be dismantled with the gel matrix attached to the light-sensitive (or patterned) electrode. The hydrogel produced is self supporting and free standing patterned gel films may be obtained simply by peeling it off from the electrode. The film is stable in aqueous solution and stays intact for months. An example of such a free standing gel is shown in FIG. 2(b).

In addition to the substrate-supported and self-supporting gel films described above, a "Lift-Off" processes may be used to obtain polymeric films and/or composites that are detached from the light-sensitive (or patterned) bottom electrode. In one example a vinyl siloxane coated ITO coverslip is used as an electrode for the LEAPS assembly cell. The vinyl siloxane coating allows covalent tethering of the gel film on the ITO electrode. Beads, suspended in a solution containing all ingredients required for subsequent in-situ gel formation, are assembled in designated regions of the light-sensitive (or patterned) electrode using an AC-electric field at a given voltage and frequency.

Figure 4A:
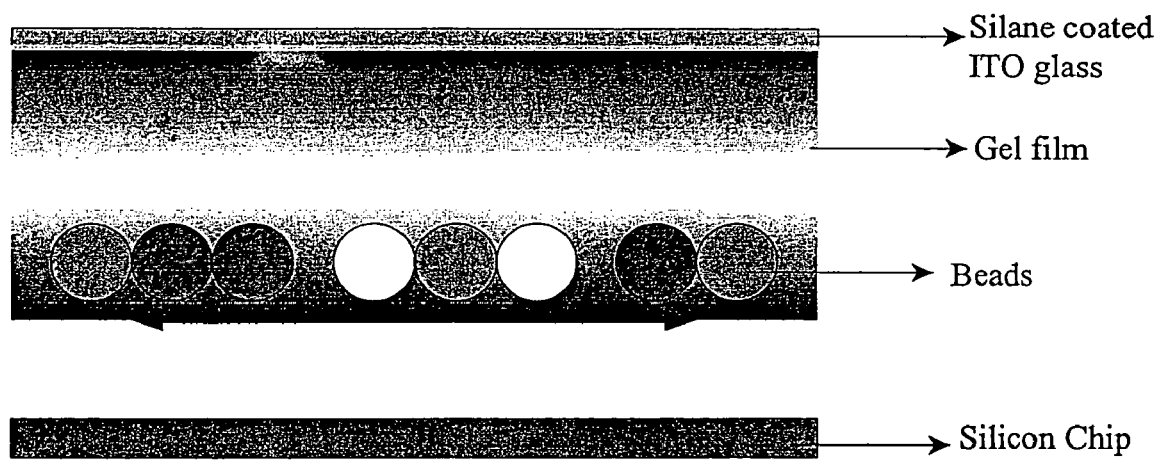
FIG. 4(*a*) is an illustration showing a flipped gel-particle composite film.

Keeping the field switched on, the LEAPs cell may, for instance, be irradiated with UV-light from a 150 W Hg source for ~3 minutes. Afterwards, the UV illumination and field are switched off and the LEAPS cell is opened by separating the bottom silicon electrode from the top ITO electrode: the covalent attachment of the gel to the top electrode ensures that the gel remains adhered to the top electrode and readily separates from the bottom electrode. By "flipping" the substrate-attached gel film, beads displaying receptors capable of binding the molecules of interest are located at the outer, exposed surface of this "flipped" gel ("FlipGel"). Thus, the diffusion length of the molecules to migrate from the solution above the gel to the bead surface is small compared to that in the case of regular gels (see FIG. 4(a)). An assay is then conducted on the gel-embedded bead array by exposing the gel to the solution containing analyte molecules of interest.

Figure 4B:
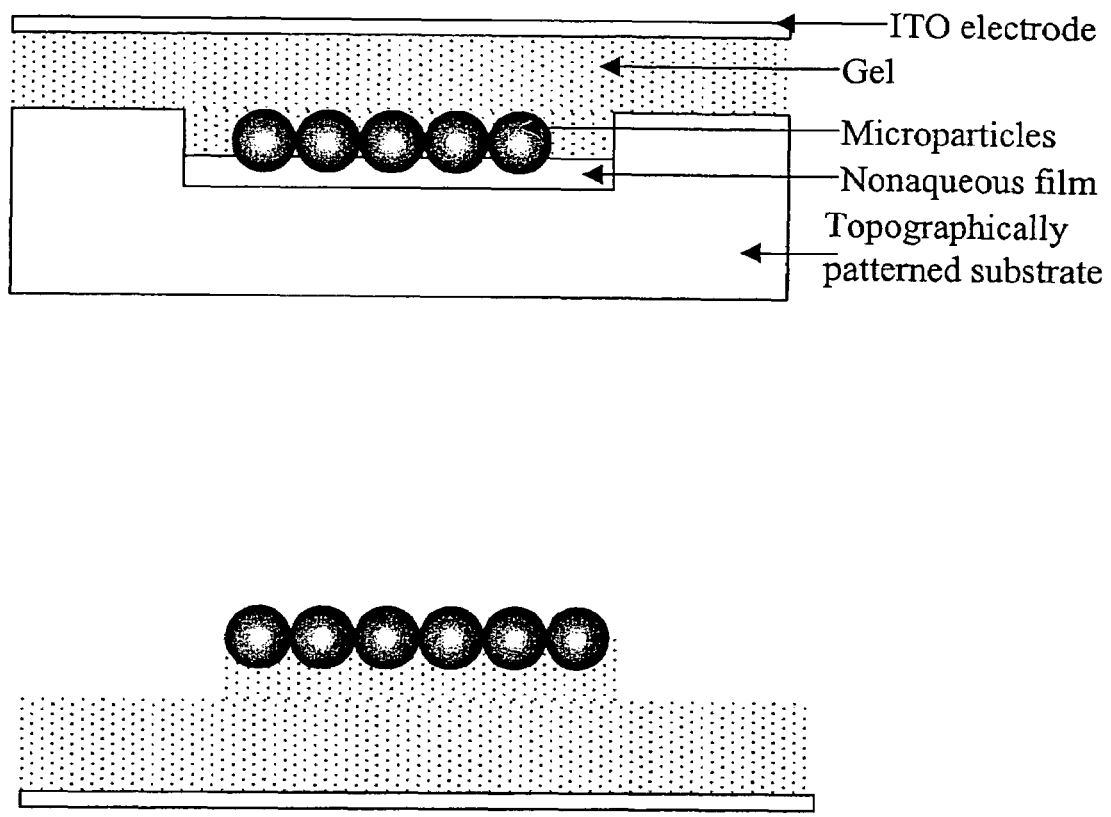

In certain other embodiments, the position of the bead array relative to the outer bounding surface of the embedding gel film may be controlled by assembling the microparticle array on a topographically patterned electrode surface exposing designated recesses of defined depth containing a non-aqueous phase that is non-miscible with an overlaid aqueous phase containing the microparticles as well as the chemical constituents required for gel film formation in accordance with the previous protocols (see FIG. 4(b)). Upon application of the requisite AC electric field, microparticles assemble within the designated recesses in such a way as to permit particles to remain partially submerged within the organic phase deposited into the recesses prior to assembly. Following assembly, gel formation is initiated in the manner described; however, the immiscibility of the two layered phases ensures that polymerization is confined to the aqueous phase, thereby leaving embedded microparticles partially exposed.

Figure 5:
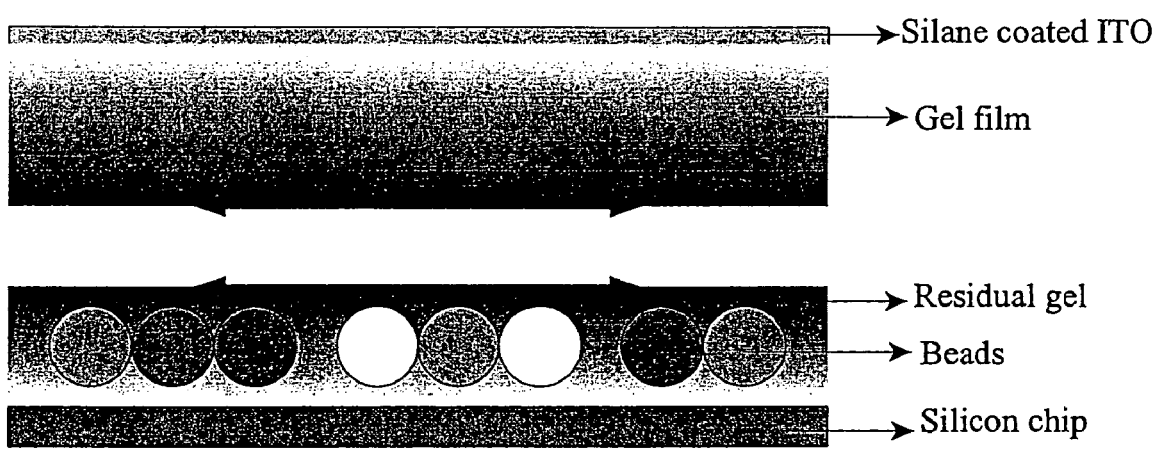
FIG. 5 is an illustration showing a cleaved gel-particle composite film.

In certain other embodiments, a cleaved gel is prepared, following the same principle as FlipGels. The basic differences are that a) the monomer concentrations used in the polymerization reaction are smaller (for example, ≦5% by weight) and b) the time of irradiation is shorter. Under these conditions, the degree of polymerization is not uniform throughout the thickness of the cell. Typically, the degree of polymerization and crosslinking is highest near the top electrode (e.g., ITO electrode) and progressively grows weaker as one approaches the bottom electrode (e.g., silicon chip). After gelation, on disassembling the LEAPS cell and pulling the two electrodes apart, such a gel typically fractures at a plane very close to the substrate surface (see FIG. 5). Thus, a layer of gel remains attached to the ITO-coated coverslide while the silicon retains the rest of the gel containing the assembled bead arrays. The silicon chip can now be used for a variety of assays with the assay solution location directly on top of the gel. In this case, the diffusion length of the molecules is reduced from that of a regular gel because the cleavage usually occurs just over the plane containing the bead array, leaving beads more accessible to molecules present in the solution above the gel.

Figure 6:
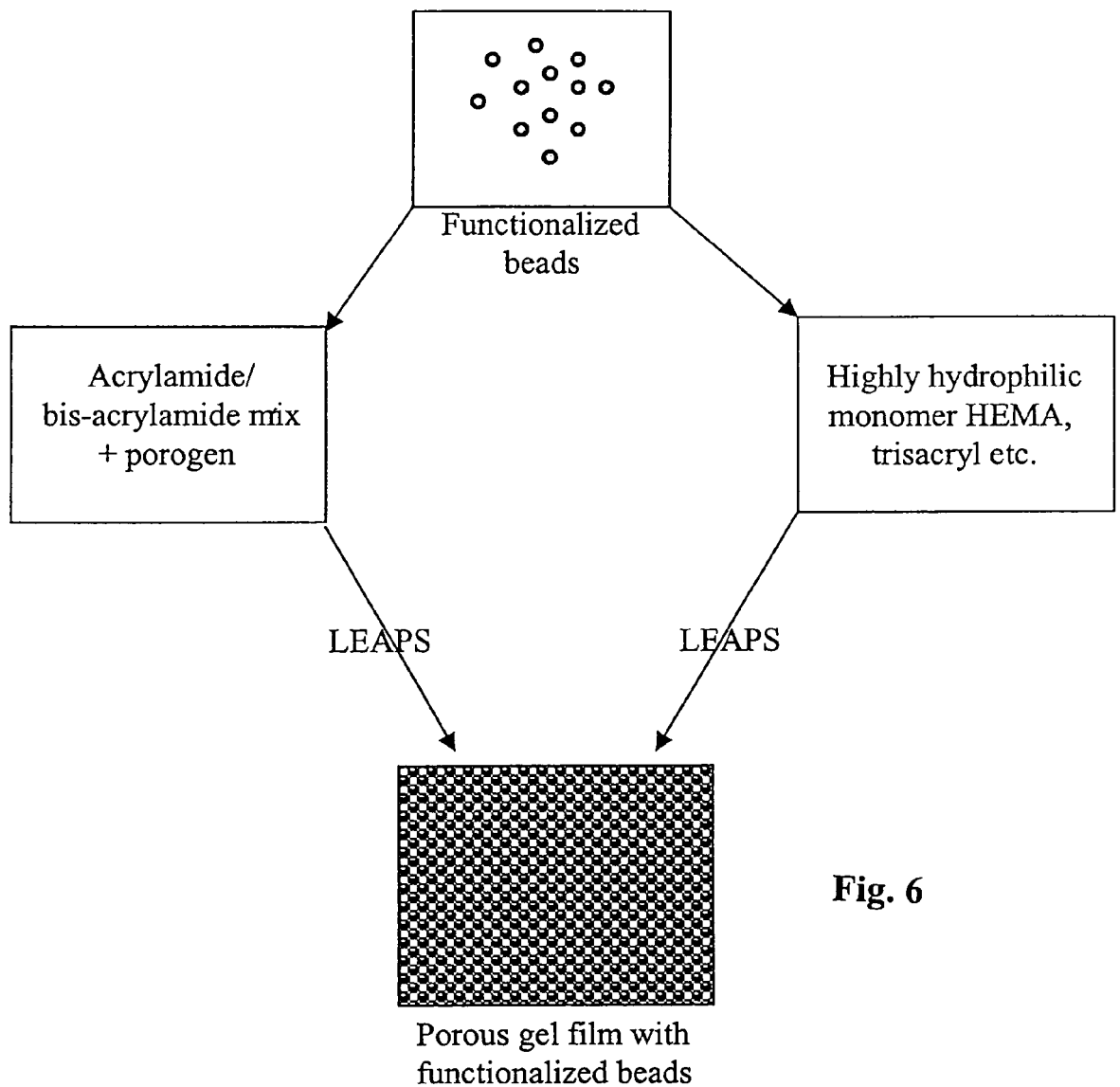
FIG. 6 is an illustration showing two examplary processes for produce porous a gel-particle composite film.

Gels of the present invention may be porous. Polyacrylamide gels, for example, have typical pore sizes ranging from a few nm to 15-20 nm in highly diluted formulations. To facilitate the penetration of large DNA fragments and other molecules into gels, macroporous polyacrylamides may be prepared by polymerizing in the presence of preformed polymers such as poly(ethylene glycol)(PEG), polyvinyl pyrrolidone (PVP), hydroxymethyl cellulose (HMC) etc. (Righetti, P. G. and Gelfi, C. 1996. J. Chromatogr. B. 699: 63-75.). Highly hydrophilic monomers, such as trisacryl may also be used to produce highly porous gels (Gelfi, C., et al. 1992. J. Chromatogr. 608: 333-341). FIG. 6 illustrates the protocol to form a porous gel using preformed polymers.

Reversible Immobilization of Microparticles within Gel Films

Figure 7:
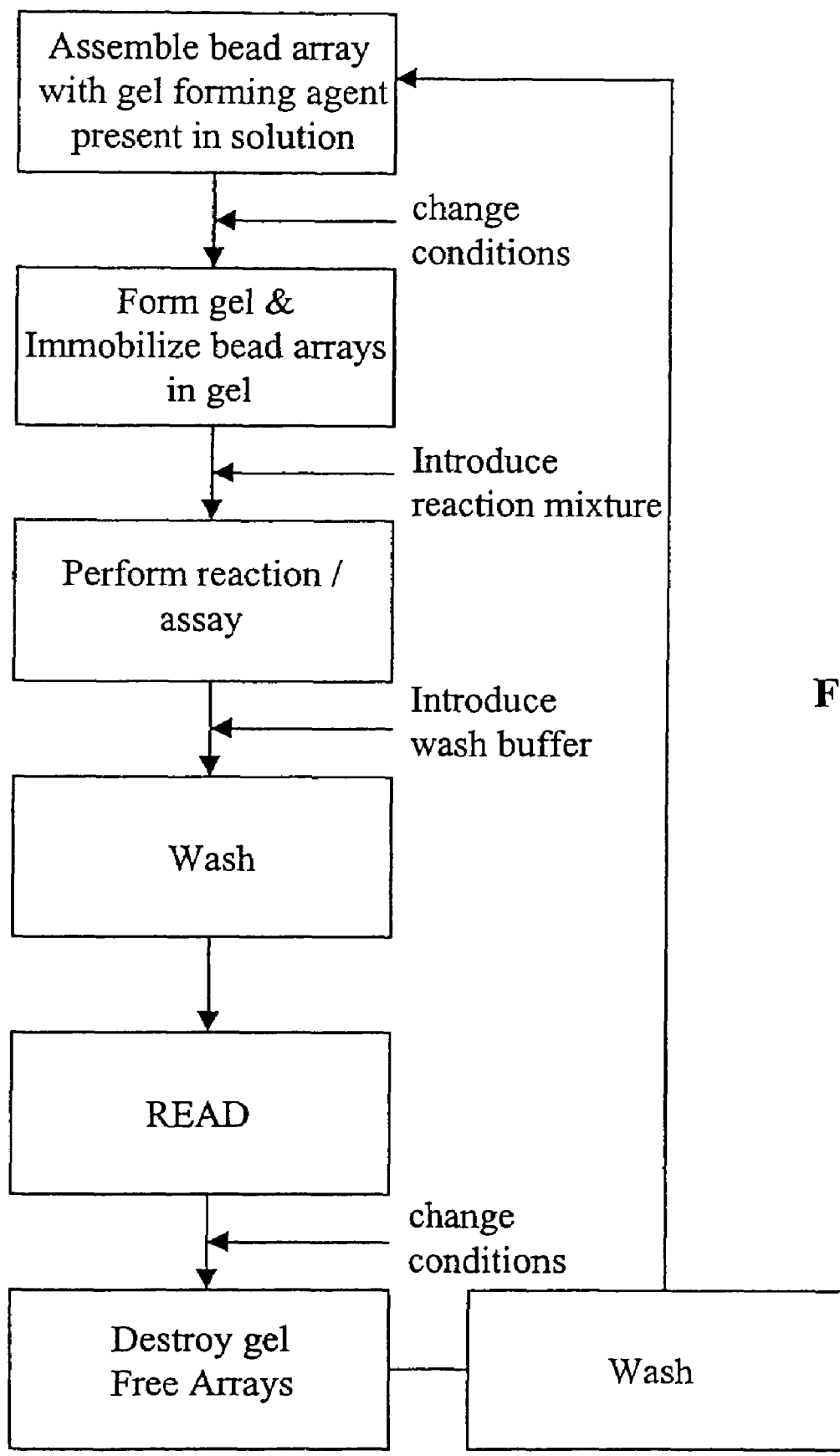
FIG. 7. is an illustration showing a process to produce a gel-particle composite film by reversible gelation.

So far, the process of forming polymeric films and polymer-film composites involved synthesis of chemically crosslinked polymers. The process of forming composite gel-particle films can, however, easily be extended to include physically gelling systems such as block copolymer gels, agarose gels, gelatin gels etc. Such gels consist of polymeric networks held together by physical rather than chemical crosslinking. The reversible gelation of such systems may, for example, be triggered thermally with the system existing as a sol at a high temperature and transforming into a gel on cooling and vice versa. The reversibility and the capability to form and immobilize bead arrays on cue allows to carry out a on-chip bioassay dynamically. An example of such a scheme is shown in FIG. 7.

EXAMPLES

The present invention will be better understood from the Experimental Details and Examples which follow. However, one skilled in the art will readily appreciate that the specific methods and results discussed are merely illustrative of the invention described in the claims which follow thereafter.

Example 1

AC Electric Field-Mediated Formation of Patterned Gel Films

LEAPS is carried out in a fluidic microcell formed by sandwiching a double-sided Kapton spacer of ~100 μm thickness (between a 1 cm×1 cm silicon chip (n-type, capped either by a uniform or a lithographically patterned thin $SiO_2$ layer), also serving as the bottom electrode, and a glass cover slip coated with indium tin oxide (ITO) to a typical sheet resistance of 1400 Ohm Square serving as the top electrode. FIG. 1 illustrates the various components of a LEAPS microcell.

The mixture of monomers and the initiator is introduced within the LEAPS cell and the electric field is applied. The thermal free radical polymerization is then initiated by heating the cell ~40-45° C. using an IR lamp (the polymerization can also be triggered by a step change in the bias voltage from a large positive value to a small positive value). Typical parameters of the AC electric field used for this particular example are $V_{p-p}$~5-8V and ω~1 kHz. This AC electric field-mediated protocol leads to the formation of a thin layer of hydrogel in predesignated areas (low impedance regions) on a $Si/SiO_x$ substrate.

Hydrogels are formed using azodiisobutyramidine dihydrochloride as a thermal initiator at a low concentration ensuring that the overall ionic strength of the polymerization mixture falls in the range of ~0.1 mM to 1.0 mM. The hydrogels are composed of a mixture of acrylamide and bisacrylamide of varying monomer concentrations from 20% to 5% (acrylamide: bisacrylamide=37.5:1, molar ratio).

Figure 2A:
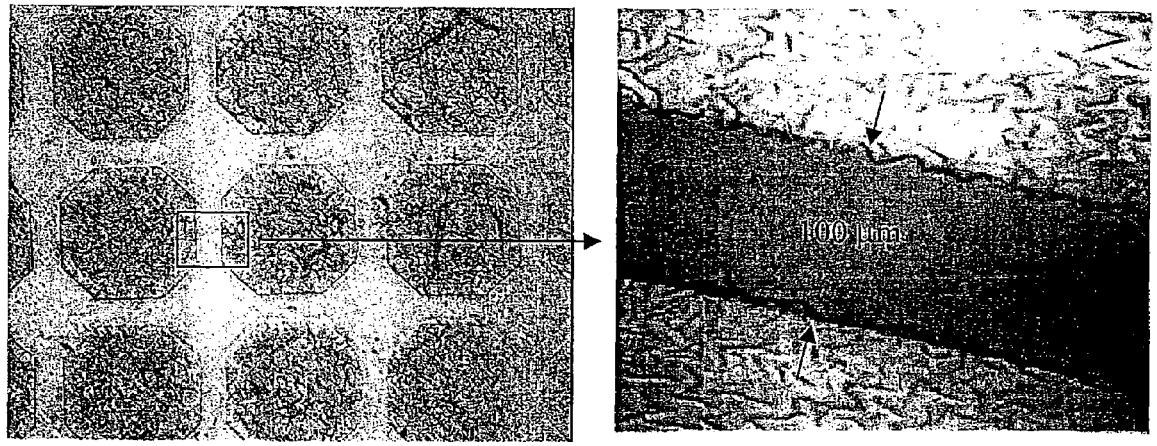
FIG. 2(*a*) contains a photograph showing a patterned gel film and a second photograph showing a close-up of a section of the film.
Figure 2B:
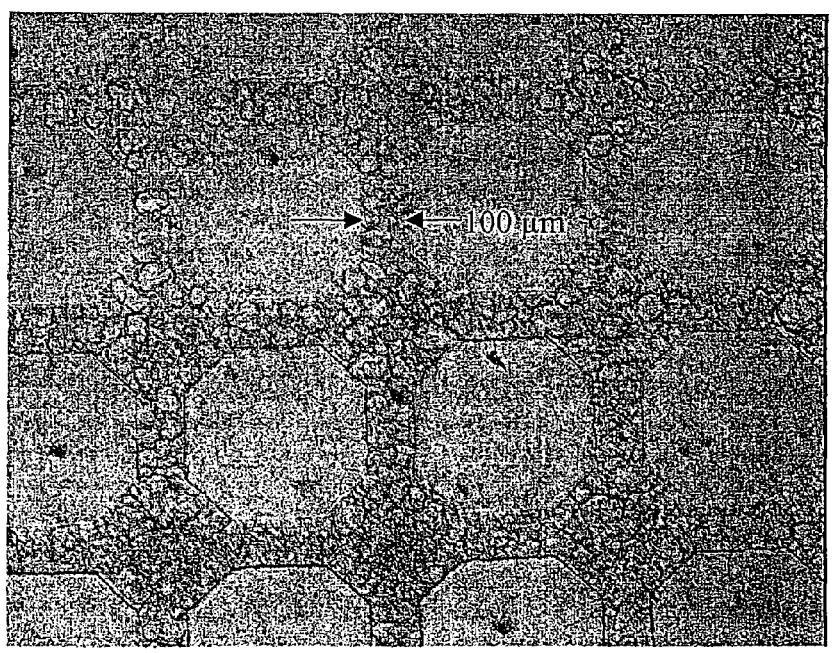

FIG. 2 illustrates a hydrogel formed on an interfacially patterned substrate under the action of electric field. The gel is formed exclusively in the low impedance regions (thin oxide) of the substrate. The wrinkled pattern seen on the hydrogel surface is caused by a mechanical instability set up in the gel during polymerization (Tanaka, T. 1987. Nature. 325:796; Warren, J. A. 1995. Spatio-Temporal Patterns, Ed. Cladis, P. E. and Palffy-Muhoroy, Addison-Wesley. 91-105).

Example 2

Preparation of Gel-Microparticle Hybrid Films

Two stage process is used to synthesize polymer-microparticle film composites. First, ordered particle arrays are formed from a microparticle suspension also containing all ingredients required for subsequent in-situ, gel formation in accordance with Example 1. LEAPS (see Example 1) is invoked to form arrays from particles suspended in a low viscosity monomer(s) dispersion mixed with an initiator in accordance with Example 1. Second, gels are formed, either via heat-initiated in-situ polymerization (Example 1) to form spatially patterned hybrid gels (see FIG. 3($a$)) or via UV-initiated in-situ polymerization to form monolithic hybrid gels (see FIG. 3($b$)), as described below.

To assemble particle arrays, AC voltages of 1-20 $V_{p-p}$ in a frequency range from 100's of hertz to several kilohertz are applied between the electrodes across the fluid gap. Fluid and particle transport and assembly are then monitored by video microscopy permitting frame capture and digitization of frames for further analysis.

Prior to assembly, particles stored in buffer are centrifuged and washed with deionized and ultrafiltered (conductivity <50 S cm$^{-1}$) distilled water three times. At the last wash, the monomer/crosslinker and initiator solution is added in amount so as to maintain the original concentration of particles. The initiator and/or the salt concentration is maintained at <=1 mM. The resulting particle suspension is applied to the LEAPS cell so as to fill the gap between the two electrodes. Anionic and cationic particles ranging from 0.5 μm to 15 μm in diameter, composed of silica, modified polystyrene or other polymers and functionalized with a variety of chemical surface groups, as well as functionalized core-shell particles obtained from a variety of manufacturers are used.

Figure 3A:
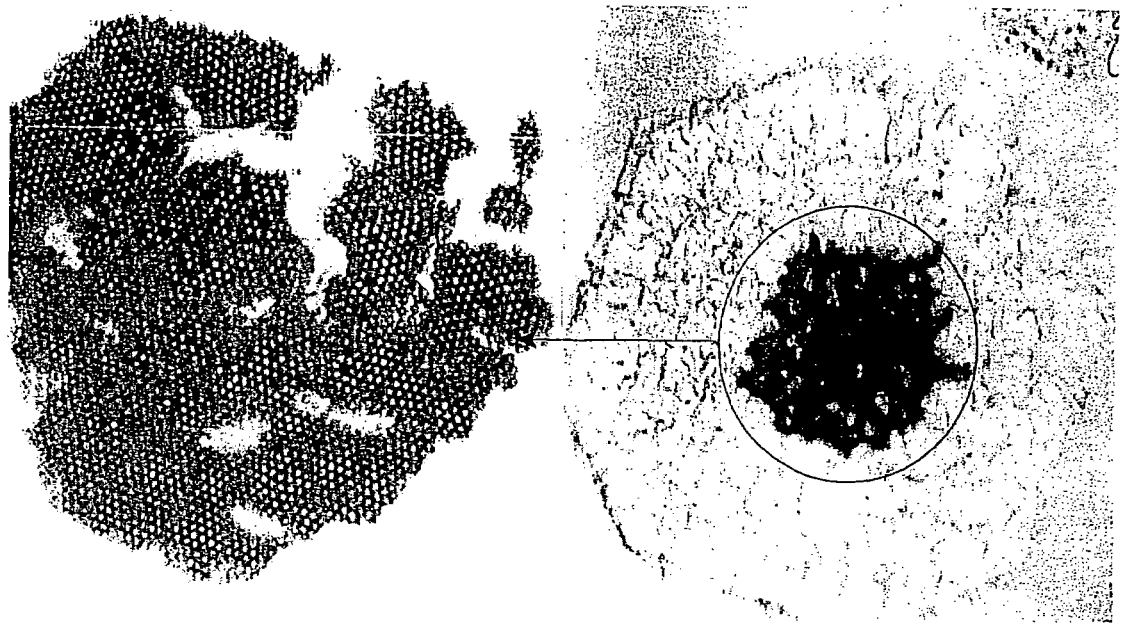
FIG. 3(*a*) contains a photograph showing a patterned gel-microparticle composite film created via thermal initiation and a close-up of the central section of the film.
Figure 3B:
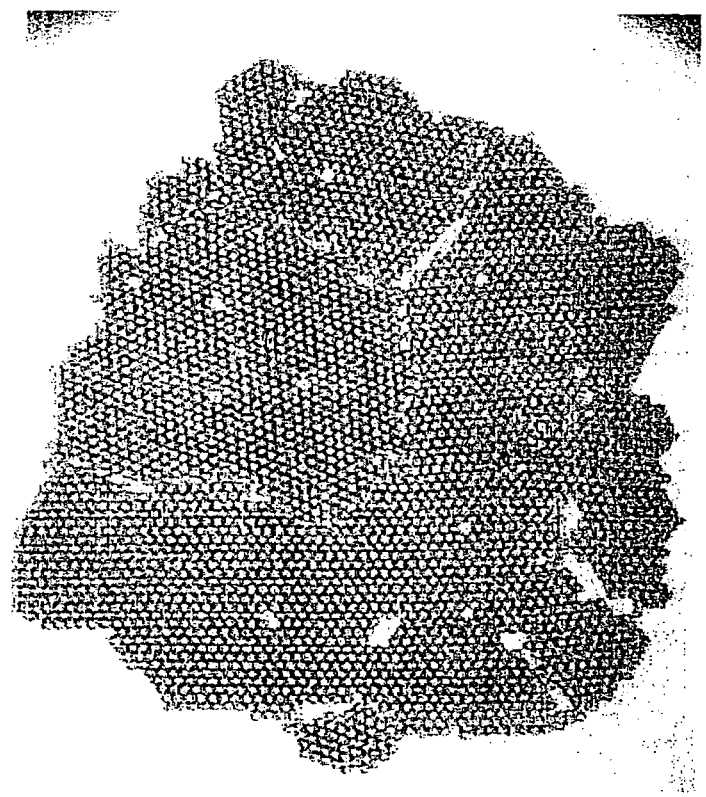

Following array assembly, and in the presence of the applied AC voltage, polymerization of the fluid phase is triggered, for example by using a mercury lamp source, to effectively entrap the particle array within the gel. A wide range of wavelengths spanning from about 250 nm to about 340 nm is suitable for the polymerization. FIG. 3 shows an example of a particle array immobilized in a polyacrylamide matrix. The concentration of the monomers was 10% and the the initiator used was a UV initiator Irgacure 2959® (2-Hydroxy-4'-hydroxyethoxy-2-methylpropiophenone, Ciba Geigy, Tarrytown, N.Y.). The initiator was added to the monomer to give a 1.5% by weight solution.

Example 3

Patterned Inorganic Materials

The ability to grow complex materials with small feature sizes is of much interest for the fabrication of structured and multifunctional films, biologically relevant heterostructures and photonic materials for optical and optoelectronic applications. Thus, processes to form patterns rapidly and directly to give geometrically as well as functionally organized structures without using complicated etching process or complicated chemical schemes can be extremely useful. In accordance with the present invention, the LEAPS-directed formation of patterned gel and gel-particle composite films provides for the fabrication of a variety of inorganic-organic, organic-organic, or fully inorganic composite structures.

Organic-organic composite—After formation of the patterned gel film on the low impedance areas of the substrate, the high impedance or the silicon oxide capped regions of the substrate can be decorated with a second polymer preferably through a process other than bulk radical polymerization (employed to synthesize the gel); for example covalent modification with silane polymers or oligomers, polyelectrolyte adsorption, hydrophobic interaction, hydrogen bonding etc. Following such a process the earlier gel layer can be lifted off, enabling the formation of complementary patterned polymer or gel film.

Figure 8:
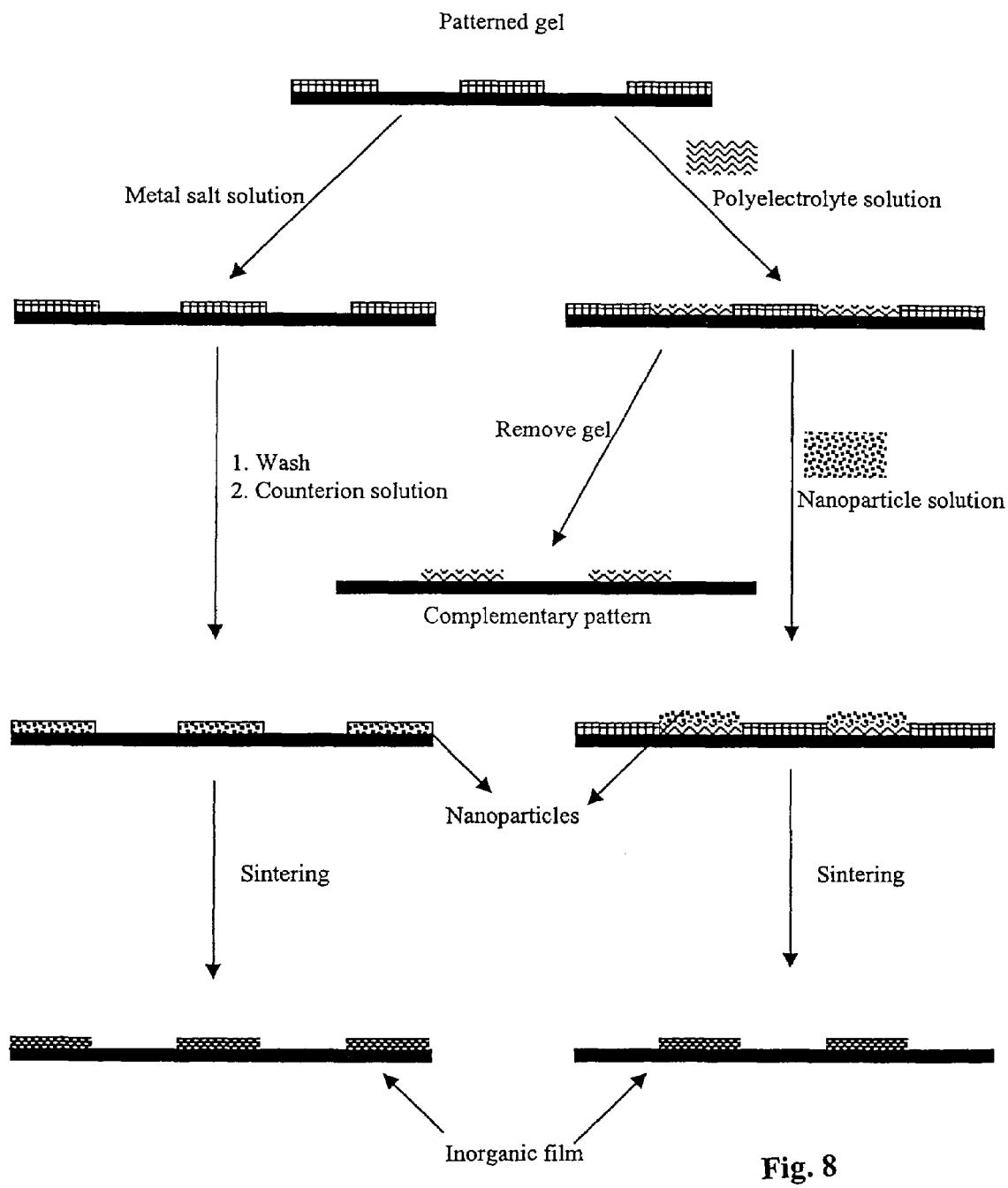
FIG. 8. is an illustration showing a process to produce inorganic-organic hybrid films.

Organic-inorganic composite—FIG. 8 outlines the scheme of the basic procedure for making metal (Au, Ag, Cu etc.), metal oxide ($Fe_2O_3$, $CO_3O_4$, NiO) or semiconductor (CdS, PbS, ZnS) nanoparticles in the patterned gel matrix. The process involves exposing the patterned gel on a substrate to a solution of a metal salt, followed by DI water rinse and exposure to reducing agent (in case of the metal) or second salt solution in other cases. The nucleation and growth of the nanoparticles take place within the hydrophilic domains defined by the gel film.

Inorganic composite—Fully inorganic structures can easily be generated from the structures generated above by calcining at high temperatures so as to burn off the organic component.

Example 4

Interconnections

The realization of interconnections in the form of electrical, optical or chemical conduits in small devices represents a critical aspect of the realization of integrated electronic, optoelectronic or biochemical processors. The methods of the present invention permit the assembly of linear microparticle assemblies in accordance with LEAPS, either under illumination or on patterned EIS interfaces, and their subsequent immobilization, for example by embedding within a gel matrix as described herein.

Electrical Conduit—Following completion of the assembly of metal core/polymer shell particles into linear configurations, rapid heating of the silicon substrate, for example by exposure to pulsed laser light, will melt away the polymer components and fuse adjacent metal cores. Of interest in this application will be particles containing solid metal (Cu, Ni) cores or particles containing metal nanoclusters dispersed into a polymer matrix which may be prepared by methods known to the art.

Optical Conduit—Within a linear assembly of glass particles, illuminated with focused light, particles will guide scattered or emitted light to their respective nearest neighbors. Thus, individual beads may be illuminated by focused laser light and can serve as secondary sources to illuminate adjacent particles within the linear assembly.

Chemical Conduit—Following completion of the assembly of polymer particles into linear, circular or other desired configurations, particles are permanently immobilized on the substrate, for example by non-specific adsorption, this structure serves as a positive mold around which a gel matrix is grown which is the lifted to reveal complementary negative surface relief; such structures can be closed by fusion with a substrate or another gel and can serve as linear conduits for the transport of biomolecules or other materials.

Example 5

Self-Supporting Magnetic Gel Films

Free standing gel microparticle hybrid films similar to those described in the detailed description section are prepared using functionalized and superparamagnetic microparticles or a mixture of superparamagnetic particles with (non-magnetic) color-encoded and functionalized microparticles. Incorporation of magnetically responsive particles permits the separation of the gel film from a solution containing biological sample by application of a magnetic field.

This is of particular benefit in carrying out multi-step biological assay protocols.

Figure 9:
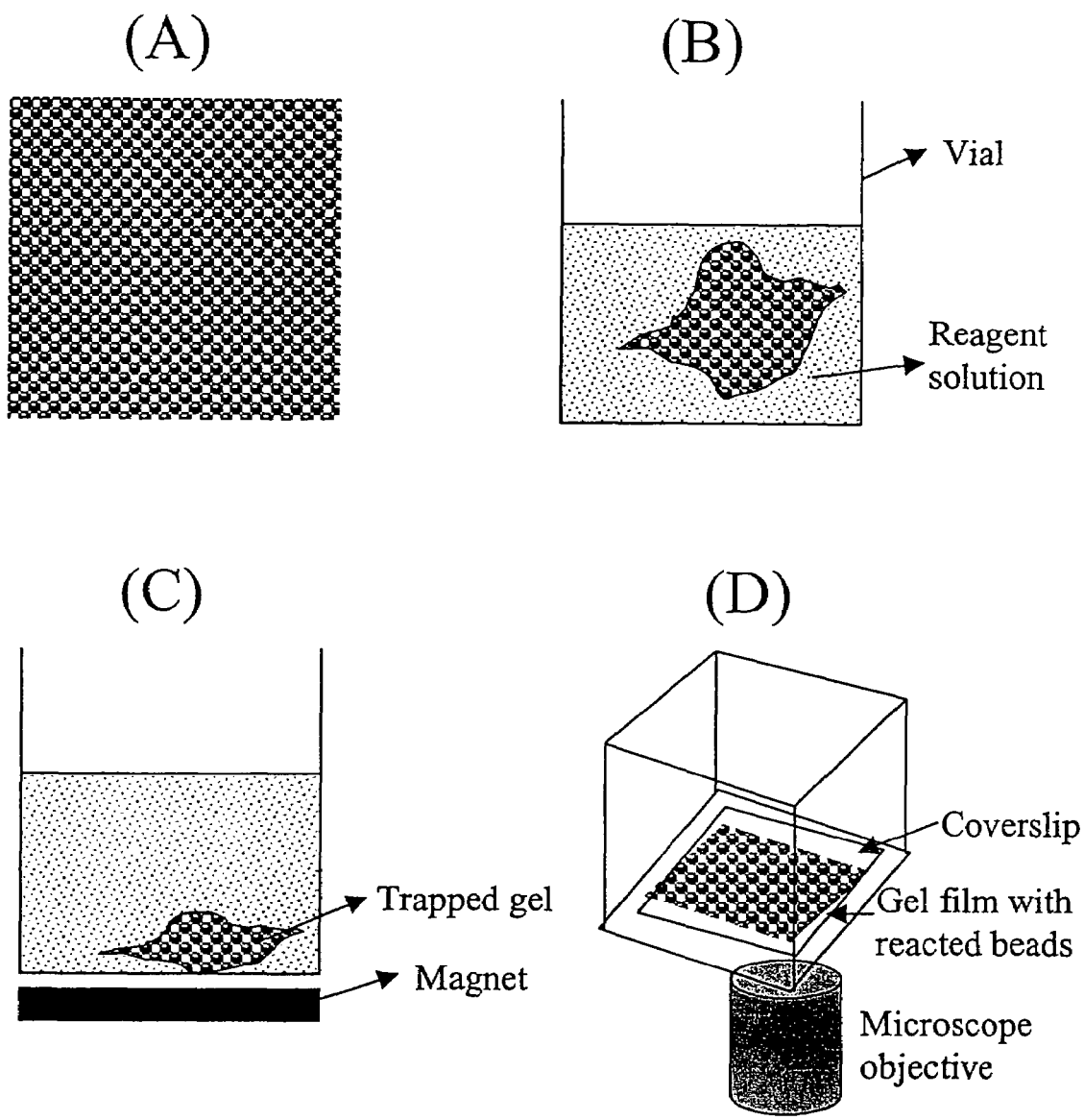
FIG. 9. is an illustration showing a process to produce and characterize a magnetic gel-particle composite film.

In a protocol enabled by the self supporting magnetic gel films of the instant invention (FIG. 9A), an in-tube binding assay probing analyte molecules present in solution by permitting capture to bead-displayed receptors is performed under conditions permitting the magnetic gel-microparticle film to remain in suspension (FIG. 9B). Following completion of the assay, magnetic separation (FIG. 9C), achieved by application of a magnetic field, permits the temporary immobilization of the gel film on a transparent surface of the reaction chamber. Following fluid and/or buffer exchange, all excess fluid is removed in the last step, leaving the hydrated gel film exfoliated on the transparent surface even in the absence of the magnetic field (FIG. 9D). Images recording the results of the binding assay may now be obtained using a microscope. In a preferred embodiment, a coverslip is positioned above the film to prevent evaporation which may lead to buckling of the film.

A combination of magnetic oligo (dt) and antibody functionalized gel matrix may also be used to carry out simultaneous capture of target cells to gel via cell-surface antigens, followed by lysing of the cell and capture of genomic DNA to magnetic and oligonucleotide functionalized microparticles within the gel.

Example 6

Hybridization Assay in Gel-Microparticle Hybrid Films

DNA hybridization assays is conducted using Oligo probe (short single stranded DNA fragments) functionalized particles embedded in gels. The probe coated particles are made as follows. Neutravidin coated beads are washed thoroughly in salinated PBS of pH 7.4. The biotinylated probes are then added to the bead suspension and mixture incubated at room temperature for 90 min. The probe-coated beads are then stored in PBS solution containing 0.01% Triton.

The targets for DNA hybridization reactions can be either single-stranded or double-stranded molecules. Single-stranded DNA of a given length and sequence were synthesized chemically (Integrated DNA Technologies, Coralville, Iowa). Double stranded DNA is a PCR-amplified product directly obtained from genomic DNA of patient samples. The PCR product is produced using fluorescence-labeled primers. After preparation, the primers are removed by a PCR purification kit (Qiagen) and the resultant solution can be used in the assay. Single stranded DNA can also be prepared from double stranded sample by digesting the antisense strand. For this purpose the antisense primers used in PCR amplification have to designed with a phosphate group at the 5' end. A strandase enzyme is then used to digest the antisense primer. In either case, the DNA at the end of the process in suspended in Tris-EDTA buffer and the concentration is determined using UV optical density measurements.

Before hybridization, the double stranded DNA has to be denatured to yield single strands. For this, the DNA is diluted with Tris EDTA buffer and heated in a sand bath at 95 C for 1 min. It is stored in ice before use. It is then mixed with an equal volume of tetramethylammonium chloride to yield a desired concentration of DNA for the reaction.

Two types of beads, internally stained with different fluorescent dyes and each bearing a different probe, are used for the reaction. One of the probes used is a prefect match with the target strand while the other sequence represents a deletion of 3 bases.

The beads are washed three times with distilled water and finally suspended in 5% monomer solution and initiator concentration as described earlier. The beads are assmpled into arrays in a LEAPS cell using 4 V peak to peak AC voltage and frequency 500 Hz. After assembly, the cell is irradiated with UV light for ~3 min. This will yield a Flip Gel which is then used for hybridization. The Flip Gel is attached gel-side up to a polished silicon wafer using single-sided tape. 1 ul of target containing 100 ng/ul dna was diluted using 24 ul of TE and 25 ul of 2×TMAC. From the resultant solution 10 ul was added to the gel for reaction. The wafer was enclosed in an air-tight wafer holding container, sealed and set on a shaker at 50 rpm in an oven at 55 C. The reaction was conducted for 30 min. At the end of the procedure, the gel was washed twice in 1×TMAC equilibrated at 55 C.

Figure 10:
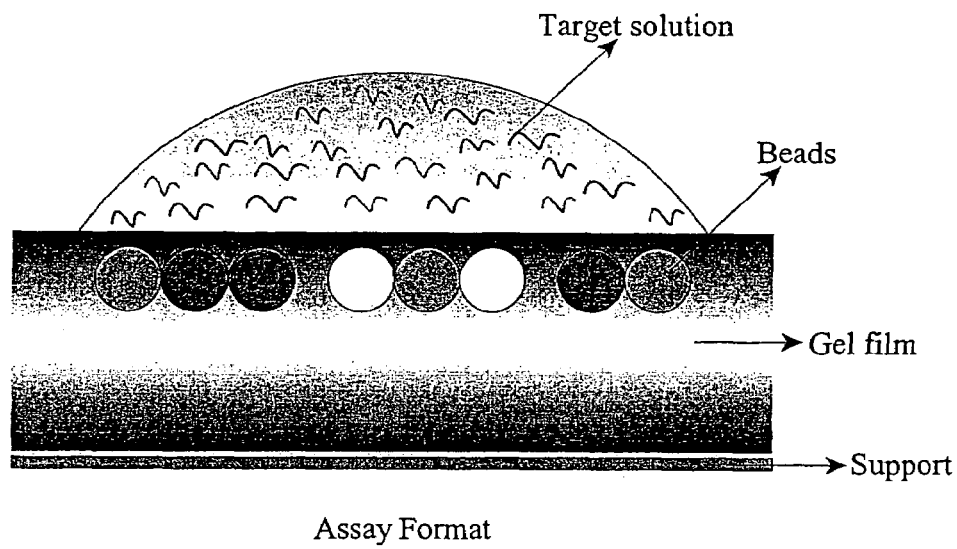
FIG. 10. is an illustration showing a DNA hybridization assay using a flipped polymer-gel composite film.
Figure 10:
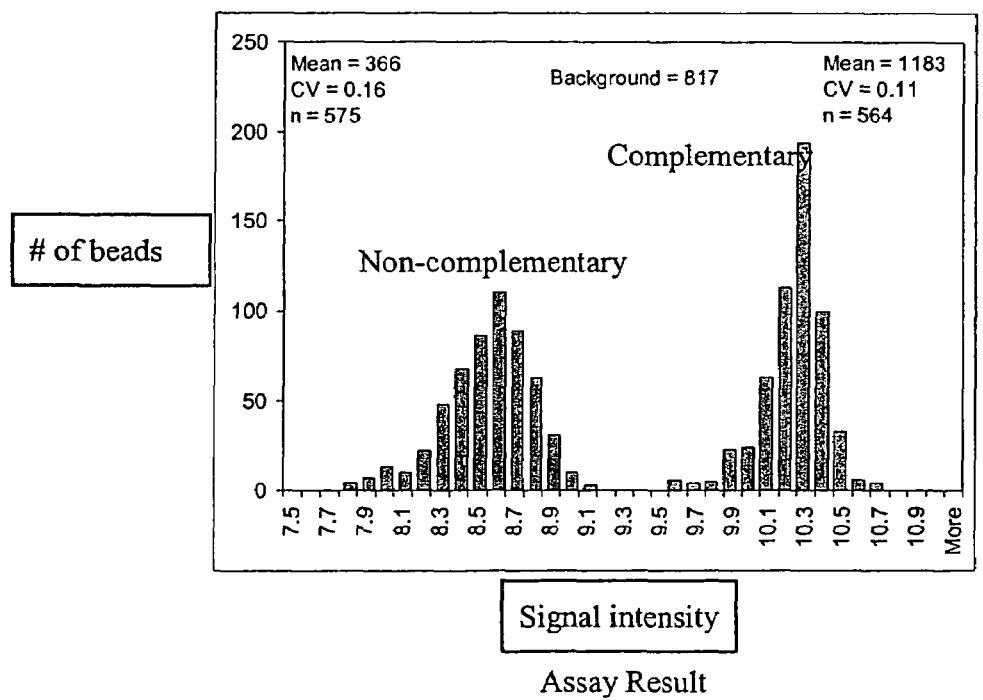

The gels are prepared for imaging by applying a coverslip on them. Images are taken in the bright field and the Cy5 channels (probes labeled with Cy5). To distinguish the two different types of particles in the arrays, images are also taken at two other color channels appropriate for the internal encoding dyes. The set of four images are then analyzed to yield the assay results (see FIG. 10)

Example 7

DNA Electrophoresis and Hybridization in Gel-Microparticle Hybrid Films

Figure 11:
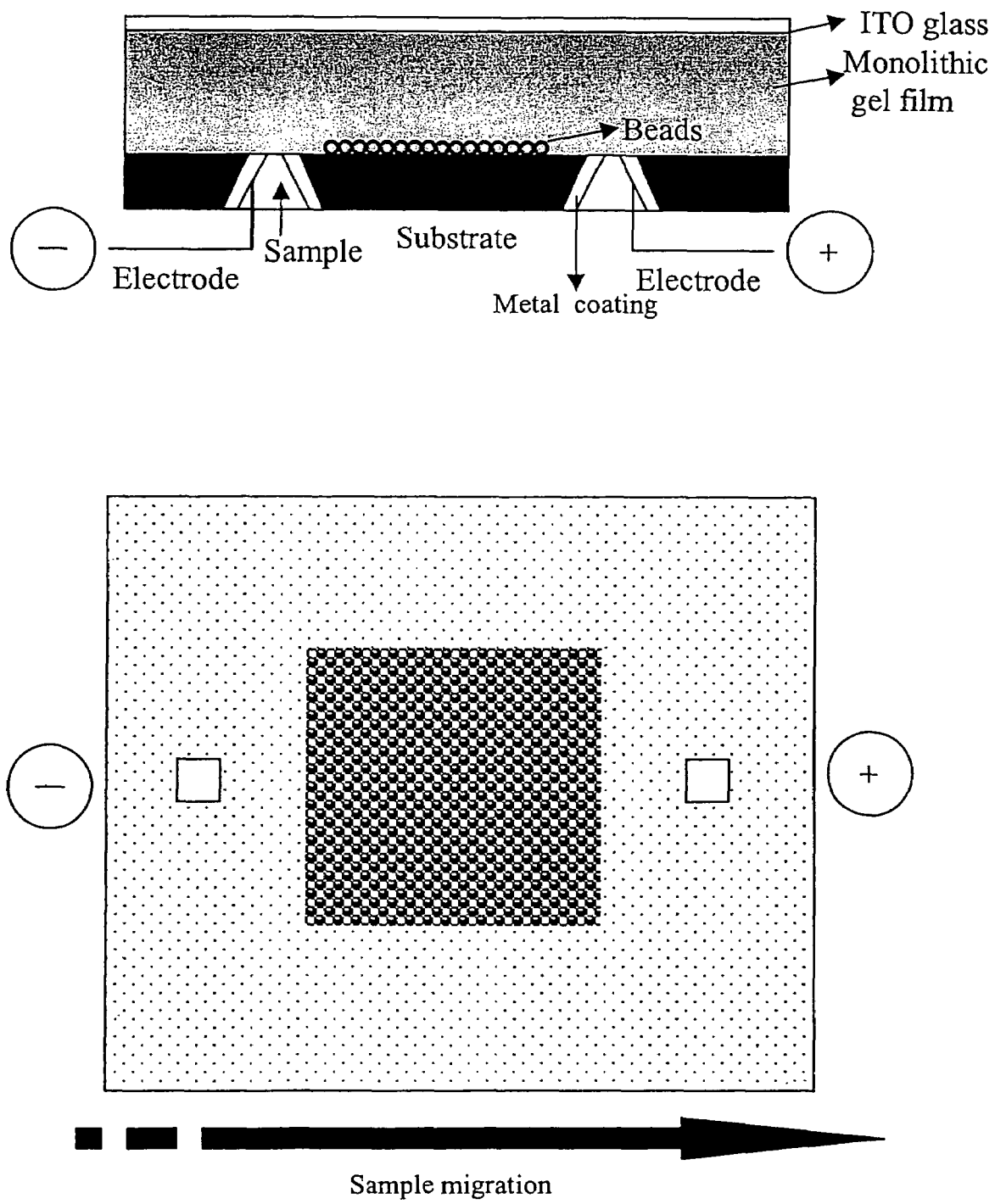
FIG. 11. is an illustration showing electrophoretically assisted DNA hybridization.

One method of performing rapid nucleic acid hybridization assays in the gel-microparticle hybrid films involves the use of D.C. electric fields to induce electrophoresis of target nucleic acid strands. This is especially relevant in case of large target fragments whose diffusion inside the gels are expected to be low. Typically the samples for analysis are denatured and electrophoresed through the gel-microparticle hybrid films, as the complementary single-stranded nucleic acid targets contact the capture probe (oligo) functionalized beads, they hybridize and are quantitatively immobilized on the microparticle surface. The non-complementary strands does not hybridize with the capture probe and migrate through the gel unimpeded. The hybridization is detected using luminescent labels associated with the sample nucleic acid. FIG. 11 two different possible geometries for carrying out electrophoretically assisted hybridization in gel-microparticle hybrid films.

Example 8

Immunoassay in Gel-Microparticle Hybrid Films

Protein assays are readily performed on supported gels, self-supporting gels, Flip Gels and Cleaved Gels. An example of immunoassays performed is the binding reaction between Mouse IgG and Goat Anti-Mouse IgG. For this reaction, the beads used in the reaction are surface-coated with the Mouse IgG. For this purpose, nutravidin-coated particles of size 3.2 µm are incubated overnight with the Mouse antibody (SigmaChem) in a phosphate buffer solution of pH 7.2. After the coating process, the particles are washed thoroughly with PBS containing bovine serum albumin.

The target molecules of goat anti-mouse IgG are labeled with a monofunctional fluorescent dye Cy5.5 (Amersham). The NHS-ester-containing dye attaches to the amine groups of the IgG by following a manufacturer supplied protocol. The dye and the IgG molecules are incubated for 1 hr at pH 9.3. The free dye is then separated from the labeled molecules using a gel filtration column and phosphate-buffered saline as the separation buffer. The concentration of IgG in the sample and the number of dye molecules per molecule of IgG is calculated.

Two types of particles are used for the reaction, one for the assay and the other as a negative control. They are distinguished by the use of internal encoding dyes which have excitation and emission at different wavelength from those of Cy5.5. One of the types of particles is coated with Mouse IgG as described above and the other has merely a coating of nutravidin. A mixture of these two types is spun down and washed with D.I. water containing 0.01% Triton three times. After the last spin, the particles are suspended in the monomer mixture containing 10% monomer solution and the UV-initiator in amounts described earlier. The particles are assembled in a LEAPS cell and irradiated to form a monolithic gel. Depending of the concentration and the time of irradiation, a regular, Flip Gel or Cleaved Gel is formed.

Figure 12:
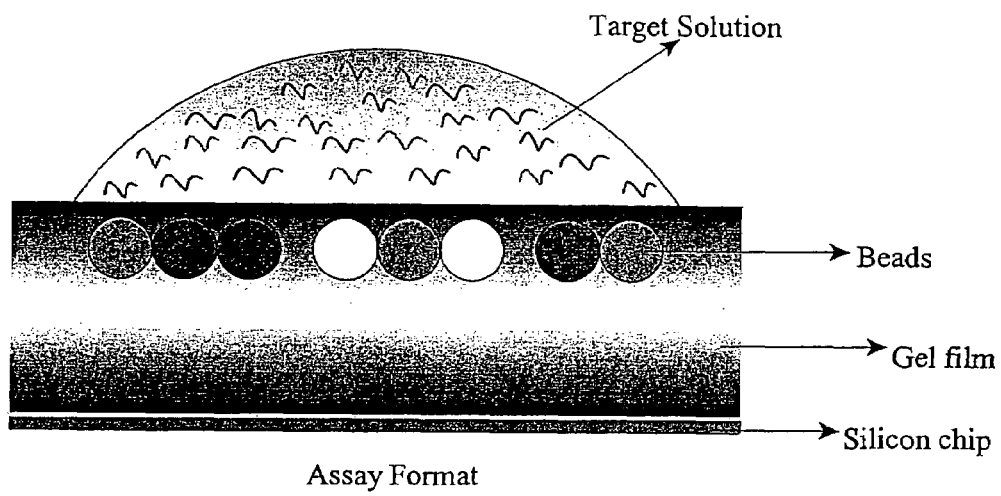
FIG. 12. is an illustration showing an immunoassay using a flipped polymer-gel composite film.
Figure 12:
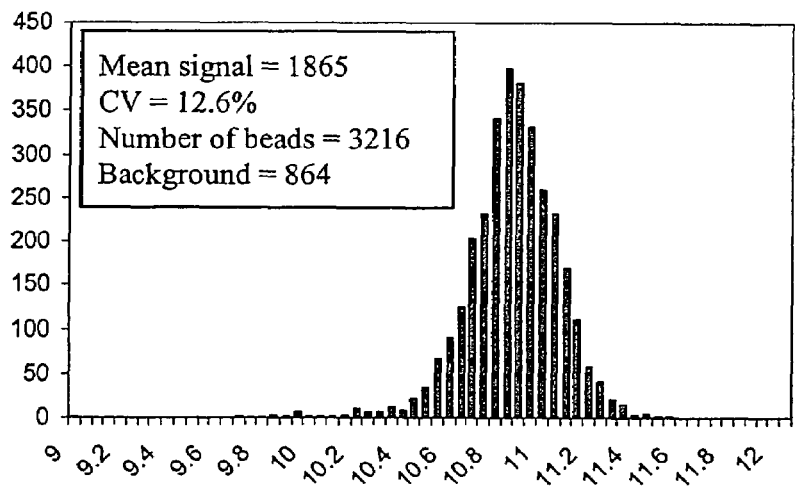

The gel is placed with the support (coverslide in case of Flip Gel, silicon chip in case of regular and Cleaved Gels) gel side up. A given volume (10 µl) of a known concentration of the Goat anti-Mouse IgG placed on the gel. The gel with the solution is then enclosed in an airtight container and put on a shaker operating at 50 rpm in an oven at 37 C for one hour. After binding has occurred, the gel os loaded with 20 µl of alkaline SDS (Tris base containing 10% SDS) for 30 min to reduce nonspecific binding. The gel is then washed with alkaline SDS twice and prepared for imaging. A coverslip is placed on the wet gel and images are taken in the bright field, and the Cy5.5 channel. To distinguish the two different types of particles in the arrays, images are also taken at two other color channels appropriate for the internal encoding dyes. The images are then analyzed to establish the mean binding intensity and the intensity distribution of each type of bead in the mixture (see FIG. 12).

Example 9

Bioanalytical Assay with Integrated Filtering and Specific Capture

The gel-microparticle hybrid film is ideal for selectively capturing specific nucleic acids or proteins from a crude mixture like whole blood or cell lysate. Typically a crude sample containing whole blood is contacted with the gel containing microparticles functionalized with capture probe molecules of interest. The red and white cells are automatically screened by the gel on the basis of their size. The complementary components from plasma bind to the capture probe coated beads.

Non-complementary components can then be easily washed off.

Example 10

Recording of Assay Images from Hybrid Films

In accordance with the methods of the present invention, a Nikon Eclipse E-600FN epifluorescence microscope equipped with 150 W xenon-arc lamp and a Nikon 20×0.75 NA air objective fitted with an optimized set of filter cubes for the selection of fluorophores was used for all measurements. Images were recorded with a cooled 16 bit CCD camera (Apogee Instruments Inc.). The exposure/integration times for the various preparations varied between 25 ms to 500 ms. User interfaced programs for analysis of images and assay results were developed using MATLAB which was run on PC. Image collection and analysis may then be performed.

Example 11

Multiple Samples per Chip

Figure 13:
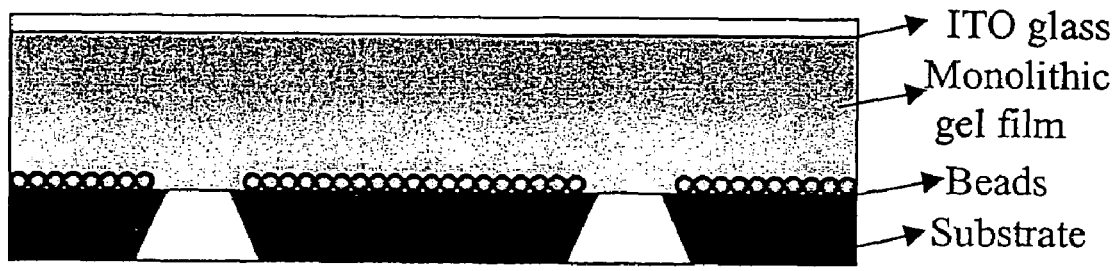
FIG. 13. is an illustration showing the analysis of multiple samples on a monolithic gel chip.
Figure 13:
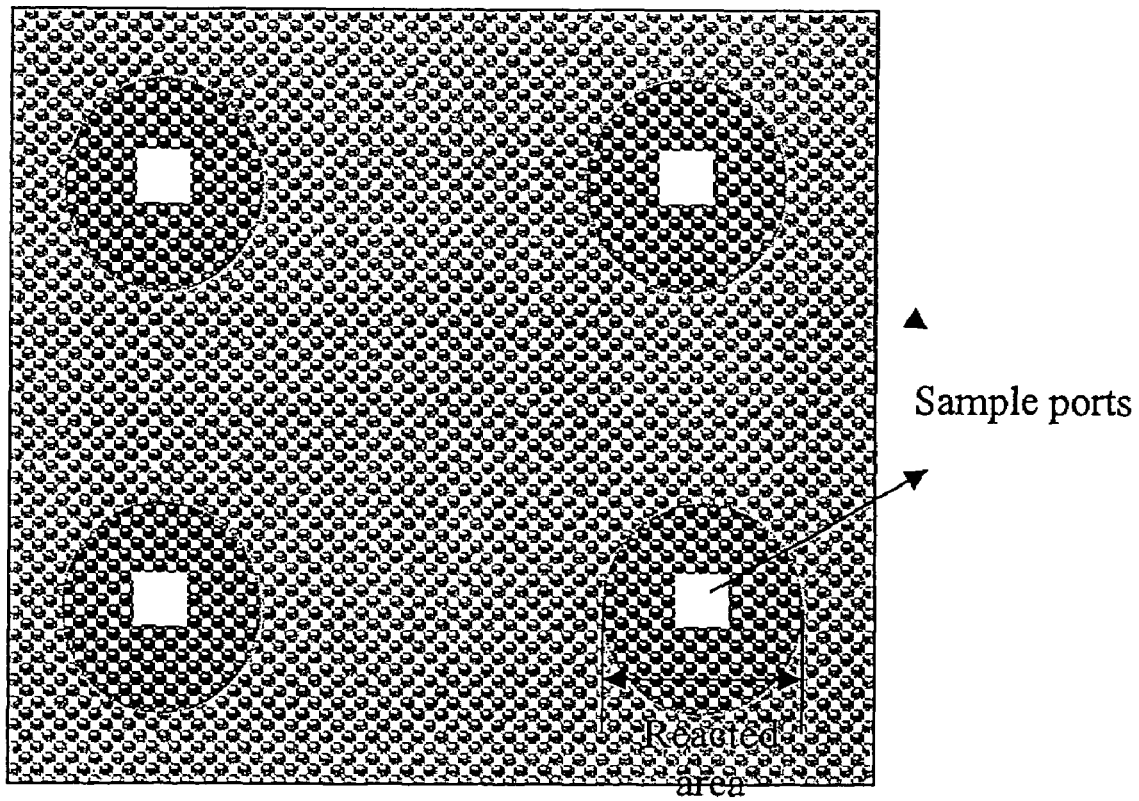
Figure 14:
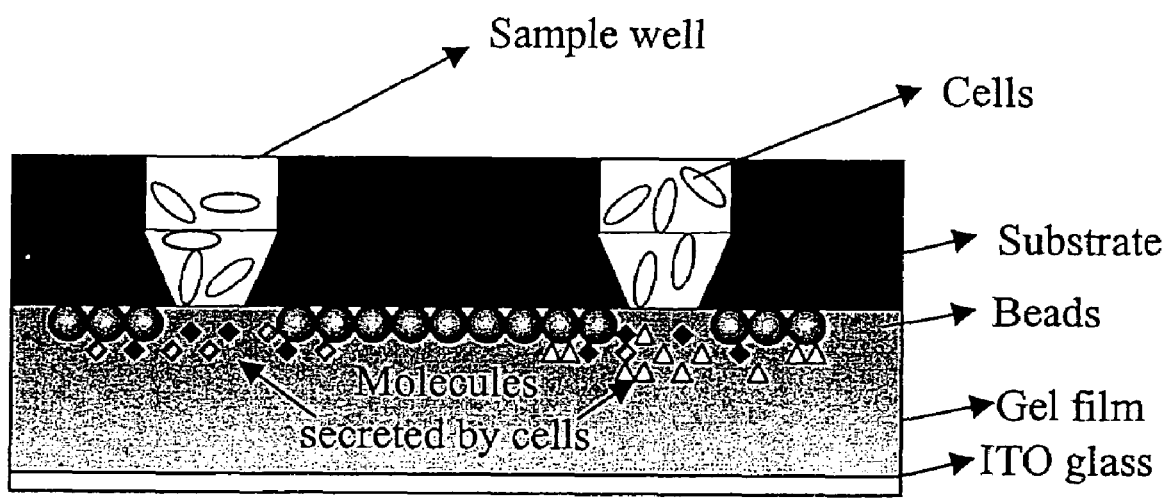
FIG. 14. is an illustration showing a process to implement a cell-bead heteroreactor.

FIG. 13 illustrates a method of carrying out multiplexed assays for multiple samples using the same monolithic gel film containing multiple bead arrays. A gel film containing bead arrays is synthesized (as described in Example 3) on an interfacially patterned silicon chip into which through holes have been made at four corners (choice of this geometry is arbitrary and is chosen here for illustrative purposes only, in principle a wide variety of designs and number of holes can be chosen). The samples are added by pipetting through the back of the chip, and the sample is allowed to spread diffusively and react with the surrounding particles as shown in FIG. 13. Depending on the length of the incubation time the area of the reacted patch will vary (Area~tD, where t reaction time and D diffusion coefficient of the target in gel).

Example 12

Cell-based Heteroreactor

A cell-bead heteroreactor is constructed on a silicon substrate containing etched through-holes serving as fluidic interconnects. First, a gel-microparticle composite film is formed in accordance with Example 3 in the fluidic compartment defined by (the front side of) the silicon electrode and the ITO-coated glass electrode. Next, suspensions of cells are introduced into the tapered etched through-holes on the backside of the silicon electrode. Molecules secreted from cells within these microwell structures are now allowed to diffuse into the gel where they are detected by capture to functionalized beads within the previously assembled array. Alternatively, cells within the microwells may be lysed, and released genomic DNA may be enzymatically fragmented to allow sufficiently small fragments to diffuse into the gel where they are captured by hybridization to functionalized beads within the previously formed array while large constituents of the lysate are kept out. This second structure can remain open, and may be fashioned to exhibit the dimensions and form factors, for example of a 1536-well microplates; alternatively, a second fluidic compartment may be formed by (the back side of) the silicon electrode and a third delimiting planar substrate to permit microfluidic transport of cell suspensions.

Example 13

Co-Assembly of Heteroparticle Arrays

Figure 15:
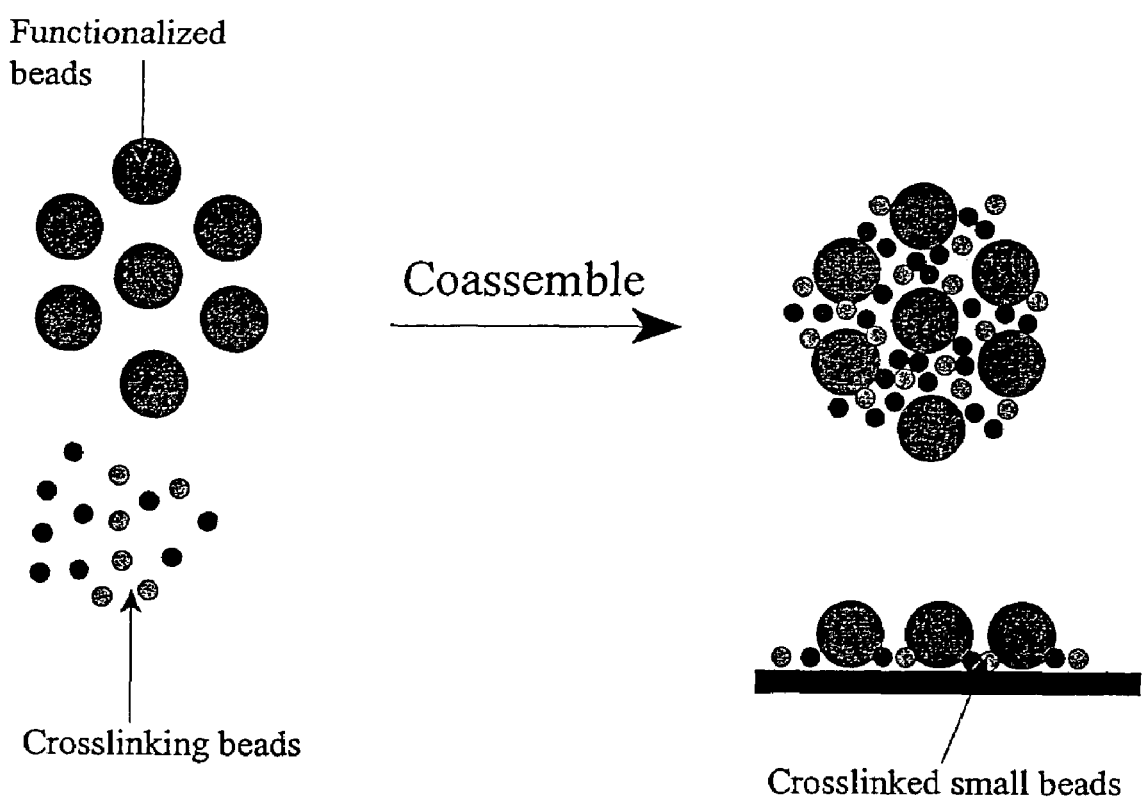
FIG. 15. is an illustration showing a heteroparticle arrays.

LEAPS enables the co-assembly of a binary mixture of smaller beads along with larger assay beads in designated areas of the substrate (FIG. 15). Once arranged in an array format the smaller beads then undergo two-dimensional crosslinking since they contain either complementary charge or reactive groups. The two-dimensional crosslinked aggregate created in the process acts as an inert mold for the larger assay beads which are thus immobilized. The advantages of the protocol include the ease of implementation, control of spatial localization and good immobilization efficiency.

Example 14

Fabrication of an Enzyme Sensor by Directed Self-Assembly

In accordance with the methods of the present invention, the combination of LEAPS-mediated active assembly of an array of functionalized microparticles and the chemical synthesis of a polymeric gel film permits the in-situ synthesis of a variety of sensors.

Figure 16:
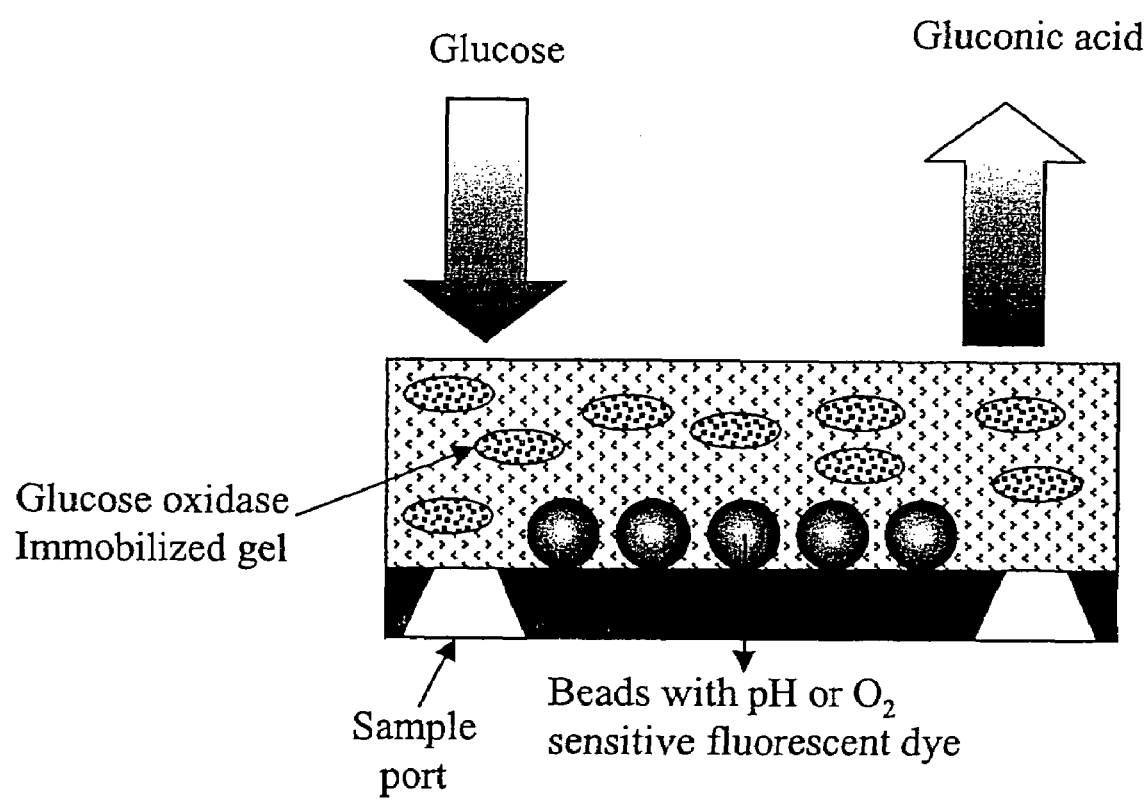
FIG. 16. is an illustration showing a glucose biosensor.

Thus, given a fluidic microreactor composed of patterned silicon/silicon oxide chip and ITO-coated glass electrodes arranged in sandwich geometry as illustrated in FIG. 1, a glucose sensor based on a gel-microparticle composite film is constructed by the following sequence of steps where, in a preferred embodiment, the silicon electrode contains a set of access ports illustrated previously in FIG. 13. The resulting sensor (shown in FIG. 16) utilizes the enzyme glucose-oxidase immobilized covalently in the gel film, with microparticles functionalized or loaded with pH-sensitive or oxygen-sensitive fluorescent dyes.

1—inject solution containing
  functionalized particles displaying pH-sensitive or oxygen-sensitive dyes known to the art
  reaction mixture containing precursors and ingredients for gel formation
  functionalized glucose oxidase
2—apply AC electric field to trigger LEAPS and produce microparticle array(s)
3—trigger gel formation by UV-initiation of polymerization to form patterned or monolithic gel film incorporating functionalized glucose oxidase
4—remove electric field and UV illumination
5—inject (glucose-containing) sample into space below patterned silicon chip to initiate diffusion of sample into gel matrix; in the presence of glucose, the following reaction occurs

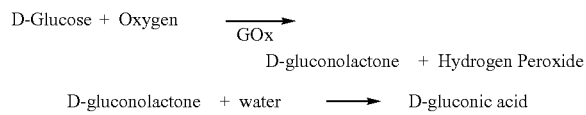

6—monitor reaction shown below by recording fluorescence intensity from microparticle array; reduced oxygen levels or the reduced pH in the local gel environment, and their effect on the bead-anchored dyes, serve as an indirect indication of glucose concentration.

Example 15

Fabrication of a Gel-embedded Planar Array of Vesicles

There is a growing interest in developing miniaturized sensing, sampling and signal amplifying structures coupled with an analytical measuring element to carry out a variety of bioassays. The sensing component typically reacts or interacts with an analyte of interest to produce a response that can be quantified by an electrical or optical transducer. The most common configurations use immobilized biomolecules on solid phase supports while another less common approach uses living microorganisms or cells or tissues as the sensing structure.

Unilamellar vesicles are composed of a single lipid bilayer shell that encloses an entrapped aqueous compartment; methods have been described to prepare giant unilamellar vesicles whose size approaches that of cells. Such vesicles are attractive as ultra-small reaction vessels or "artificial organelles" in which the reaction is confined and separated from the external medium. Vesicles containing reconstituted integral membrane proteins provide a synthetic chemical structure to study the function of such proteins including many cell surface receptors. In addition, the surface of such vesicles can be decorated with a variety of receptor moieties mimicking a natural cell and allowing complex biochemical reactions and/or interactions to be studied (Lasic, D. D. Ed. "Liposomes: From Physics to Applications", $1^{st}$ ed., Elsevier Science B.V.: Amsterdam, 1993.)

Given a mixture of vesicles of two types, each containing one of the reactants of a reaction of type A+B—>C, two of vesicles of different type may be brought into close proximity, fore example, by forming a close-packed planar array, and may then be fused using a pulsed electric field in accordance with methods known to the art, in order to form a larger vesicle in which the reaction A+B—>C is now performed. In a preferred embodiment, A may represent an enzyme, B a substrate, C the product of the enzyme-catalyzed reaction. This reaction scheme may be generalized to involve more than two reactants.

Vesicles entrapping a single functionalized and encoded microparticle can be prepared by methods known to the art. Using methods of the present invention, microparticle encoded, gel-embedded vesicle arrays may be prepared (see Examples 1, 2, 3 and 4) to provide for a synthetic assay format in which the function of multiple cell-surface receptors such as ion channels may be quantitatively characterized.

Figure 17:
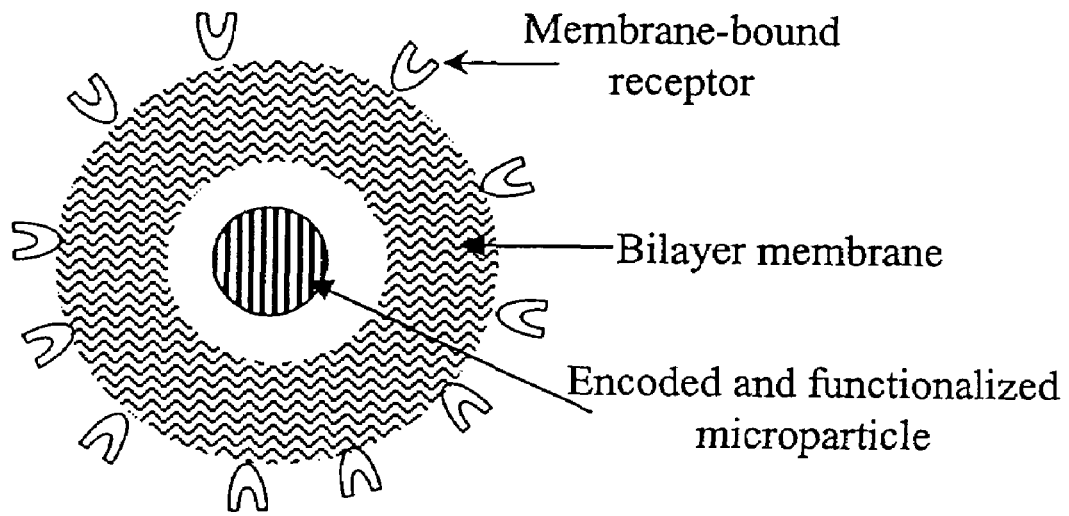
FIG. 17. is an illustration showing microparticle-encoded vesicles embedded in a gel film.
Figure 17:
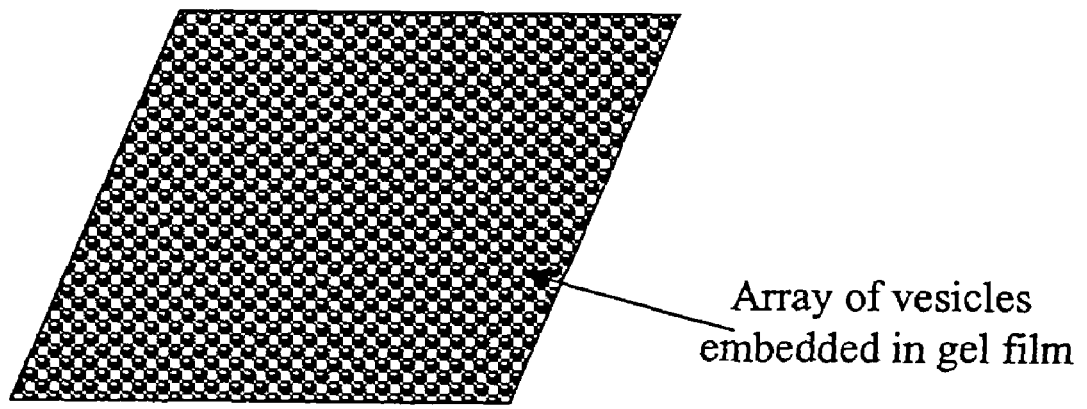

A variety of complex biochemical assays may be performed using such a composite structure. As illustrated in FIG. 17, an array of vesicles displaying multiple types of receptors, each vesicle displaying only one type of receptor and containing a corresponding fluorescently stained and functionalized microparticle, is immobilized in a thin gel film using methods disclosed herein; the fluorescent color of the particle is used to determine the identity of the receptor on the vesicle. In addition, the microparticle, is also functionalized on its surface with a measuring element such as an environmentally sensitive fluorescent dye to indicate a change in the internal aqueous compartment of the vesicle following a binding event on its surface.

Example 16

Gel-Embedded Cellular Arrays and Their Use in Cell-Based Functional Assays

The entrapment and immobilization of viable cells in various polymeric matrices, natural or synthetic, including polyacrylamide (Vorlop, K. et al. Biotechnol. Tech. 6:483 (1992)) have been reported, primarily in connection with biocatalysis (Willaert, P. G. et al. (Eds.), "Immobilized living cell systems: Modeling and experimental methods." Wiley, N.Y., 1996). Polymeric matrices can provide a hydrated environment containing nutrients and cofactors needed for cellular activity and growth. To minimize mass transfer limitations, methods of the present invention may be used to immobilize arrays of cells in a thin and porous gel film.

In accordance with the methods of the present invention, the process of forming a composite structure containing cell arrays entrapped in a patterned or monolithic gel film consists of two stages. First, ordered cell arrays are formed from a cell suspension also containing all ingredients required for subsequent in-situ gel formation in accordance with Example 1. In a preferred embodiment of the array assembly process, LEAPS (see Example 1) is invoked to form arrays from cells suspended in a low viscosity monomer(s) dispersion mixed with an initiator in accordance with Example 1. Second, gels films are formed, either via heat-initiated in-situ polymerization to form a spatially patterned composite or via UV-initiated in-situ polymerization to form a monolithic composite, as described (see Example 2).

The immobilized cell array system of the instant invention is useful for a variety of assay formats. For example, to analyze and quantify several molecular targets within a sample substance, the methods of the present invention provides for the means to form a gel-embedded cell array displaying a plurality of receptors (to one or more of the targets) which may be exposed to the sample substance.

Figure 18:
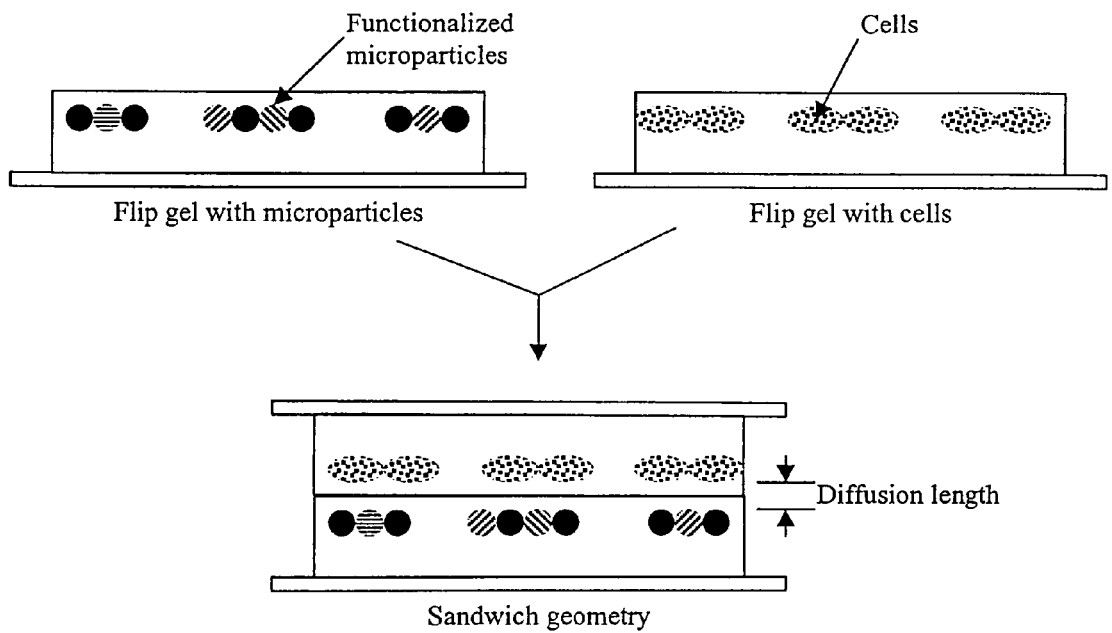
FIG. 18. is an illustration showing a gel-embedded cellular array and its use.
Figure 18:
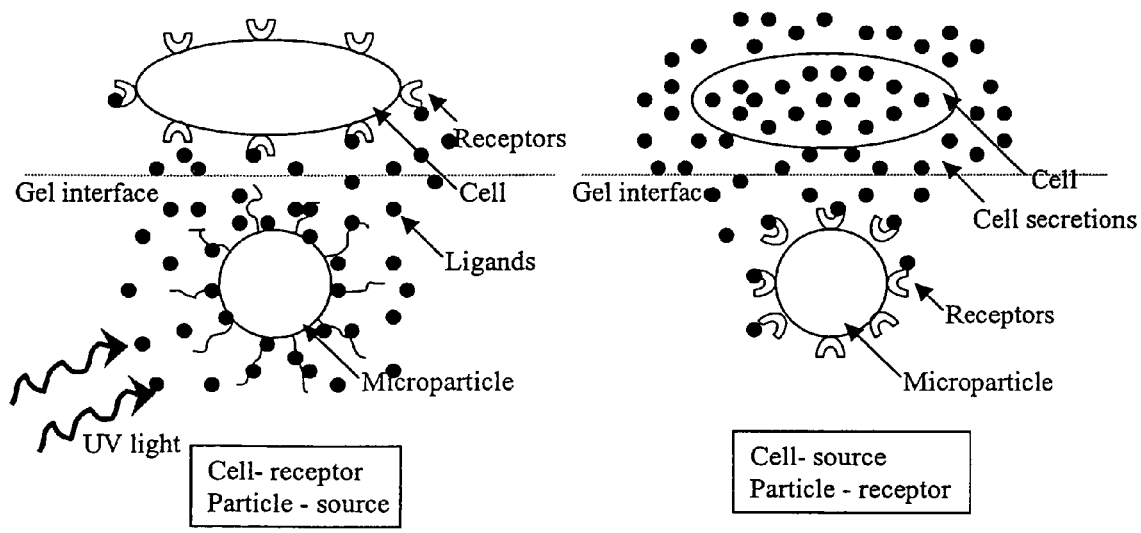

An alternative format of a functional assay, shown in FIG. 18, involves the combination of a gel-microparticle heterostructure with a gel-embedded cellular array prepared by the methods of the present invention. Embedding of cells within a thin gel film facilitates the engineering of small, functionally organized heterostuctures by avoiding the manipulation of individual cells while providing local chemistries maintaining cells in their requisite environment. The lateral spacing of cells as well as microparticles within their respective arrays is readily tuned in such a structure using LEAPS as disclosed herein.

Two separate gel films, one containing a functionalized microparticle array and the other a cellular array, are placed in direct contact in a sandwich geometry. In this configuration, particles and cells form pairs of sources and detectors of molecules to be analyzed. For example, cells can secrete molecules such as cytokines, and proximal beads within the bead array can be designed to monitor the profile, for example in a displacement assay. Alternatively, small molecules can be photochemically cleaved from an array of color-encoded beads and can be detected by monitoring the functional response of cells within the apposed gel-embedded array. The lateral patterning of the arrays as well as the short diffusion length in the vertical direction helps to prevent lateral mixing of the ligand molecules and hence enables execution ands monitoring of complex local binding chemistries.

Example 17

Characterization and Control of Diffusive Transport in Gels

Figure 19:
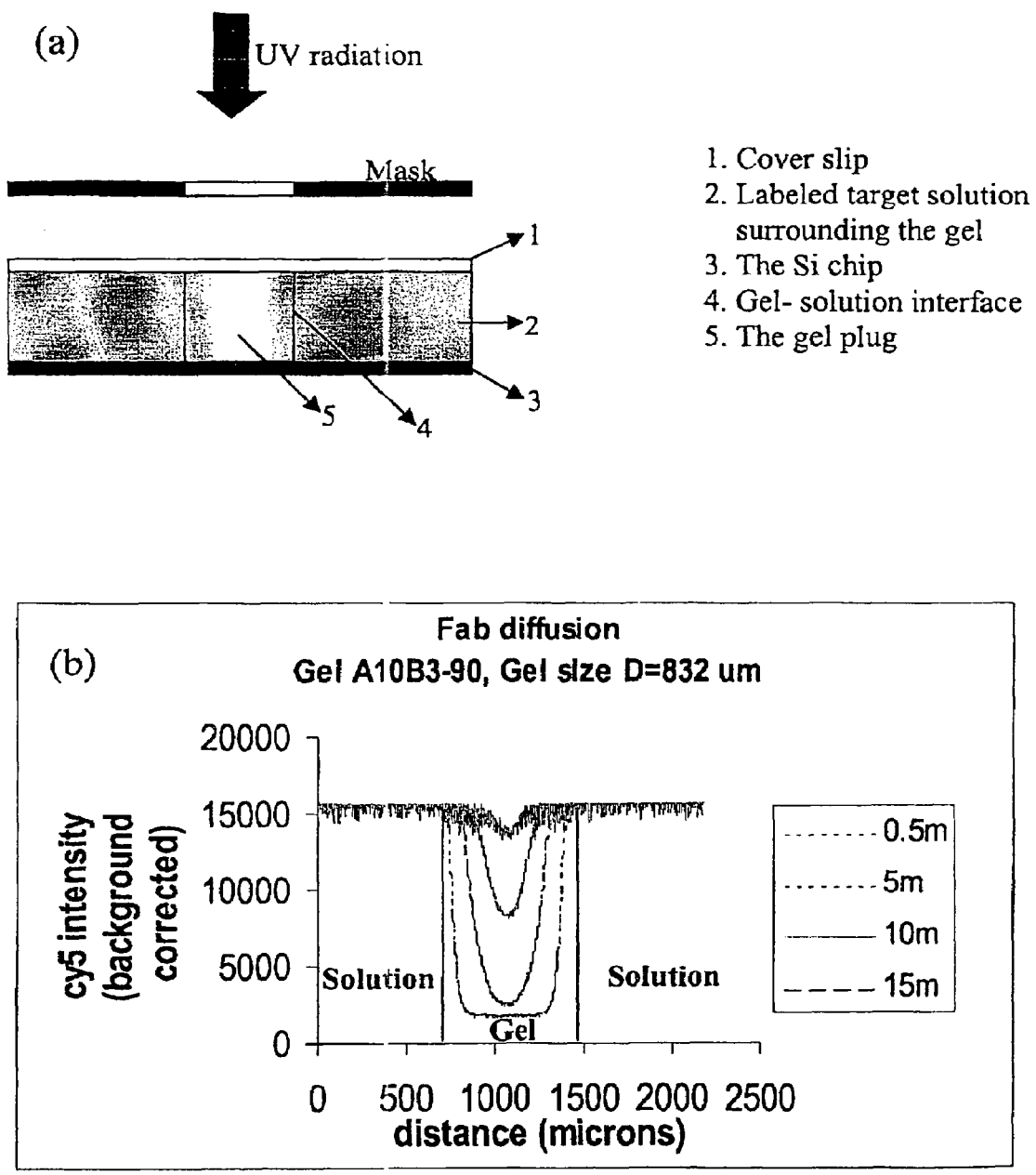
FIG. 19 shows the effect of gel chemistry and formation conditions on diffusion.

The diffusion of fluorescently tagged molecules into the gels of the present invention were studied using a sandwich cell device as illustrated in FIG. 19(a). To provide actual chemical anchoring of the gel to both the Si-chip surface and the glass coverslip both of them were pretreated using vinylmethoxysilaoxane oligomer for polyacrylamide gels, and 3-(glycidoxypropyl)-trimethoxysilane for agarose gel, respectively.

For the coating reaction a 95% ethanol and 5% water solution was adjusted to pH 5 with acetic acid. The silane coupling agent was then added to yield 2 wt % solution. Substrates (chips and cover glasses) were dipped into the solution with gentle agitation for 5 minutes. Following, the substrates were removed from the solution and rinsed briefly in ethanol. The treated substrates were cured at room temperature 24 hours.

For the formation of the acrylamide gels the monomer mixture of 10% (w/v) acrylamide, 3% (w/v) N,N'-methylene-bis-arylamide (Polysciences, Ltd, USA), 0.1% photo initiatorl-[4-2-Hydroxyethoxy)-phenyl]2-hydroxy-2-methyl-1-propane-1-one (IRGACURE® 2959, Ciba Specialty Chemicals (USA)) as well as $H_2O$ was injected into the sandwich cell. The masked cell was then exposed to an UV light source (150 W Hg) through a photo-mask for durations from 45 s up to 180 s. Following the exposure, the unpolymerized solution was removed from the cell.

For agarose gel formation, 1 µl an agarose solution (0.5% w/v) (heated to ~90 C) was carefully pipetted on the surface of a pretreated Si chip, and gently covered with a pretreated cover glass slide. Under these conditions the drop of the agarose sol deforms approximately into a cylindrical plug sandwiched between the two surfaces, which turns into a gel under the room temperature conditions within 1-2 minutes. Once formed, the gel was left undisturbed at room temperature for additional 2-3 hours to promote the covalent crosslinking between the hydroxyl groups in the agarose chains and the expoxy group present on the pretreated surfaces.

Although a few exemplary embodiments of this invention have been described in detail above, those skilled in the art will appreciate that many modifications of the preferred embodiments are possible using the novel teachings and advantages of this invention. Accordingly all such inventions are intended to be included within the scope of this invention, as defined in the following claims.

What is claimed is:

1. A method of forming a patterned polymeric film, comprising the steps of:
providing in a first plane a patterned first electrode, wherein the patterning defines areas on the first electrode surface where, under appropriate conditions, polymerization will take place, and a second electrode in a second plane;
providing a polymerization composition between said first and second electrodes; and
generating an AC electric field with said first electrode and heating the said polymerization composition, such that the combination of said first electrode patterning, heat and said AC field results in polymerization of the said polymerization composition and formation of a polymeric film in said defined areas of the first electrode, and removing the unpolymerized polymerization composition to form a pattern in the film corresponding to the unpolymerized composition which was removed.

2. The method of claim 1, wherein said patterning are such that the first electrode has a surface and an interior, and wherein either or both of said surface and interior are modified.

3. The method of claim 2, wherein said modifications are created by UV-mediated oxide growth.

4. The method of claim 2, wherein said modifications are created by surface charge patterning.

5. The method of claim 2, wherein said modifications are created by surface profiling.

6. The method of claim 1, wherein said polymerization composition has an ionic concentration of about 1.0 mM or less.

7. The method of claim 1, wherein said polymerization composition has a viscosity of about 100 cp or less.

8. The method of claim 1, wherein said polymerized film comprises non-porous, micro-porous, or macro-porous gel.

9. The method of claim 1, wherein said polymerized film comprises a hydrogel, a cross-linked alkylacrylamide hydrogel, or a hydroxyalkylmethacrylate hydrogel.

10. The method of claim 1, wherein said AC field is created from an applied voltage between 0.5 and 15 $V_{p-p}$ and wherein the frequency of said voltage is between 10 Hz and 500 kHz.

11. The method of claim 9, wherein said hydrogel is functionalized.

12. The method of claim 11, wherein biomolecules are immobilized in said hydrogel.

13. The method of claim 12, wherein said biomolecules comprise ligands, receptors, proteins, peptides, nucleic acids, or oligonucleotides.

14. The method of claim 13, wherein said nucleic acids or oligonucleotides are DNA or RNA.

15. The method of any of claims 12 wherein said biomolecules are attached to microparticles.

16. The method of claim 11, wherein probe molecules or functional co-monomers are immobilized in said hydrogel.

17. The method of claim 16, wherein said probe molecules or functional co-monomers are attached to microparticles.

18. The method of claim 1, wherein said second electrode is indium-tin oxide (ITO).

19. The method of claim 1, wherein said first electrode comprises a silicon or silicon oxide electrode.

20. The method of claim 1, wherein the method further includes forming a fluidic microcell for said polymerization composition by adding spacers between said electrodes to contain said polymerization composition.

21. The method of claim 15 wherein said microparticles are beads.

22. The method of claim 17 wherein said microparticles are beads.

23. The method of claim 1 wherein said polymerization composition comprises a monomer, a thermal initiator and a cross-linker in solution.

* * * * *